US011352632B2

United States Patent
Solomon et al.

(10) Patent No.: US 11,352,632 B2
(45) Date of Patent: Jun. 7, 2022

(54) TUNABLE TRANSCRIPTIONAL REGULATORS RESPONSIVE TO ENVIRONMENTAL TRIGGERS

(71) Applicant: Purdue Research Foundation, West Lafayette, IN (US)

(72) Inventors: Kevin V. Solomon, Lafayette, IN (US); Ethan Hillman, West Lafayette, IN (US); Kok Zhi Lee, Johor (MY); Yu Hong Wang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 90 days.

(21) Appl. No.: 16/771,704

(22) PCT Filed: Dec. 13, 2018

(86) PCT No.: PCT/US2018/065417
§ 371 (c)(1),
(2) Date: Jun. 11, 2020

(87) PCT Pub. No.: WO2019/118701
PCT Pub. Date: Jun. 20, 2019

(65) Prior Publication Data
US 2021/0180070 A1    Jun. 17, 2021

Related U.S. Application Data

(60) Provisional application No. 62/597,951, filed on Dec. 13, 2017.

(51) Int. Cl.
*C12N 15/70*    (2006.01)
*C07K 14/78*    (2006.01)
*C12N 15/81*    (2006.01)

(52) U.S. Cl.
CPC .............. *C12N 15/70* (2013.01); *C07K 14/78* (2013.01); *C12N 15/81* (2013.01); *C07K 2319/23* (2013.01); *C07K 2319/71* (2013.01)

(58) Field of Classification Search
None
See application file for complete search history.

(56) References Cited

U.S. PATENT DOCUMENTS

| 5,994,114 A * | 11/1999 | Croteau ............. C12N 15/8243 435/183 |
| 8,841,414 B1 | 9/2014 | Raucher et al. |
| 2010/0119529 A1 | 5/2010 | Furgeson et al. |
| 2013/0302861 A1 | 11/2013 | Vainstein et al. |

OTHER PUBLICATIONS

Banta, et al., Annual Rev. Biomedical Engineering 2010, vol. 12, 167-186.
Bidwell III, et al., Molecular Cancer Therapeutics 2005, vol. 4(7), 1076-1085.
MacKay, JA, et al., Biomacromolecules 2010, 11, 2873-2879.
Zhang, Y, et al., Biomacromolecules 2006, 7, 2192-2199.
Dreher, MR, et al., J. Am. Chem. Soc. 2007, 130, 687-694.
ISR_WO, Search Report and Opinion, dated 2019.

* cited by examiner

*Primary Examiner* — Suzanne M Noakes
(74) *Attorney, Agent, or Firm* — Purdue Research Foundation; Liang Zeng Yan

(57) ABSTRACT

This present patent application relates to a method for controlling a targeted gene expression with an environmental trigger useful for manufacturing a natural product or an analogue thereof biologically. In particular, the present invention discloses an expression system comprises a gene expressing for a fusion protein of elastin-like polypeptides (ELPs) and a transcription factor, wherein a targeted gene expression is regulated by the phase change of the fusion protein initiated by an environmental trigger, including changes of temperature, pH value, ionic strength or a combination thereof. The method, the expression system and their products are within the scope of this invention.

18 Claims, 8 Drawing Sheets

Specification includes a Sequence Listing.

```
                                              SEQ ID NO: 1
         Xbal                                  Start        Stop       Acul
    5'- CTAGAAATAATTTTAAGGAGGAGTACATATGGGCTACTGATAATGATCTTCAGC         -3'
    3'-     TTTATTAAAATTCCTCCTCATGTATACCCGATGACTATTACTAGAAGTCGAGCT -5'
                                BseRI                                 XhoI
         SEQ ID NO: 2
```

FIG. 5B

Acidic ELP sequence where X = V/I/E [1:3:1]   SEQ ID NO: 3

5'- CGTGGGCGTTCCGGGTATCGGTGTTCCGGGTATCGGTGTTCCGGGTGAAGGTGTTCCGGGTATCGGT
    GTGCCGGG -3'

Basic ELP sequence where X = V/H/G/A [1:2:1:1]   SEQ ID NO: 4

5'- CGTGGGTGTTCCGGGCCACGGTGTCCCAGGTGGCGGCGTACCGGGCCACGGTGTTCCTGGTGCTG
    CGTGCCGGG -3'

Neutral ELP sequence where X = V   SEQ ID NO: 5

5'- CGTGGGTGTTCCGGGCGTTGGTGTCCCAGGTGTTGGCGTACCGGGCGTTGGTGTTCCTGGTGTTGG
    CGTGCCGGG -3'

TUNABLE TRANSCRIPTIONAL REGULATORS RESPONSIVE TO ENVIRONMENTAL TRIGGERS

CROSS-REFERENCE TO RELATED APPLICATIONS

The present U.S. patent application is a national stage application under 35 U.S.C. § 371(b) of International Application No. PCT/US18/65417, filed on Dec. 13, 2018, which relates to and claims priority under 35 U.S.C. § 119(e) to U.S. Provisional Patent Application Ser. No. 62/476,894, filed Dec. 13, 2017, the content of which is hereby incorporated by reference in i entirety into the present disclosure.

TECHNICAL FIELD

This present application relates to a method for controlling a targeted gene expression with an environmental trigger. In particular, the present invention discloses an expression system comprises a gene expressing for a fusion protein of elastin-like polypeptides (ELPs) and a transcription factor, wherein a targeted gene expression is regulated by a phase change of the fusion protein initiated by an environmental trigger, including changes of the temperature, the pH value, the ionic strength, or any combination thereof.

STATEMENT OF SEQUENCE LISTING

A computer-readable form (CRF) of the Sequence Listing is submitted concurrently with this application. The file, generated on Dec. 13, 2018, is entitled Sequence_Listing_67892-02_ST25_txt. The size of the file is 49 kb. The file of Sequence_Listing_67892-02_ST25_txt, 49 kb, generated on Dec. 13, 2018, is incorporated into the instant specification in its entirety.

BACKGROUND

This section introduces aspects that may help facilitate a better understanding of the disclosure. Accordingly, these statements are to be read in this light and are not to be understood as admissions about what is or is not prior art.

Despite the considerable promise of microbes as chemical factories that produce medicine, fuels and other materials sustainably, microbes manufacture relatively few products. This is due in large part to low yields that make these systems uncompetitive with traditional chemical synthesis. Enhancing production and economic viability of such systems requires gene circuits that regulate selected enzyme expression levels to redirect excess cellular resources towards synthesis of desired products (Anesiadis, N., et al., *Metabolic Engineering* 2008, 10(5), 255-266; Solomon, K V, et al., *Metabolic Engineering* 2012, 14(6), 661-671; Solomon, K V, et al., *ACS Synthetic Biology* 2013, 2(3), 126-135; Dahl, R H, et al., *Nature Biotechnology* 2013, 31(11), 1039-1046). Investigators can further improve yields by incorporating sensor-regulator elements within these circuits to monitor, and respond to, evidence of cellular stress in order to prevent premature cell death (Zhang, F, et al., *Nature Biotechnology* 2012, 30(4), 354-359; Farmer, W R, et al., *Nature Biotechnology* 2000, 18(5), 533-537). For example, production of the antimalarial drug precursor, amorphadiene, in *E. coli* improved approximately two-fold with the introduction of a re-purposed transcriptional regulator that prevented accumulation of toxic isoprenoid intermediates[6]. Sensor-regulator elements that autonomously balance the competing demands of cellular health and production, however, are not broadly available. Current approaches addressing this issue primarily rely on large screens that identify native transcription factors, which recognize specific individual products, but regulate both targeted genes and native, non-production pathways in frequently poorly defined ways.

Thus, there is a critical need for the development of new technologies that: 1) can easily be tailored to selectively recognize indicators of cellular stress, 2) can regulate only specified gene targets at pre-specified set points of cellular stress, and 3) do not interact with native processes (orthogonality). In the absence of such technologies, it will likely remain challenging to substantially improve the economic viability of microbial chemical factories, and broaden their product portfolio to valuable production targets.

BRIEF DESCRIPTION OF THE DRAWINGS

A better understanding of the present invention will be had upon reference to the following description in conjunction with the accompanying drawings.

FIG. 5B shows the linker sequence design. The bar represents the Shine-Dalgarno sequence. Start and stop codons are highlighted in gray. Type IIS cut sites indicated with vertical line (SEQ ID NOs: 1 and 2).

FIG. 5C depicts the sequence design of base ELP 25-mers (SEQ ID NOs: 3, 4, and 5).

DETAILED DESCRIPTION

Figure 1:
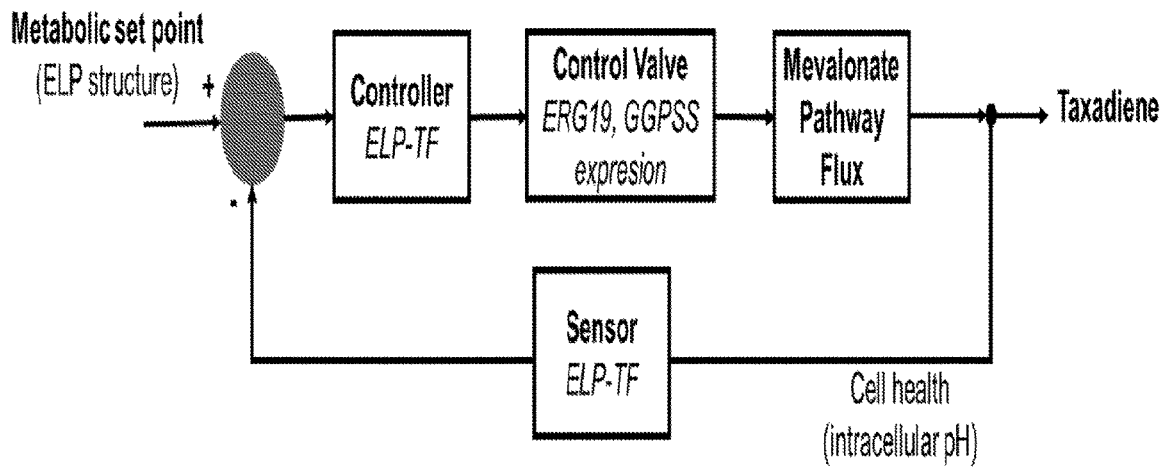
FIG. 1 depicts that ELP-Transcription Factor (TF) fusions is developed as programmable negative feedback controllers that regulate pathway flux and improve cell health for improved taxadiene production.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range. In the present disclosure, the term "substantially" can allow for a degree of variability in a value or range, for example, within 80%, within 90%, within 95%, 99%, 99.5%, 99.9%, 99.99%, or at least about 99.999% or more of a stated value or of a stated limit of a range.

As disclosed herein, a natural product refers to a product of nature, which is useful as food/feed or a supplement thereof, materials for construction or manufacture, or a therapeutics.

This present application relates to a method for controlling a targeted gene expression with an environmental trigger useful for manufacturing a natural product or an analogue thereof. In particular, the present invention discloses an expression system comprises a gene expressing for a fusion protein of elastin-like polypeptides (ELPs) and a transcription factor (TF), wherein a targeted gene expression is regulated by the phase change of the ELP-TF fusion protein initiated by an environmental trigger, including changes of the temperature, the pH value, the ionic strength, or any combination thereof. The method, the expression system and their products are within the scope of this invention.

In some illustrative embodiments, the present invention relates to a method for controlling a targeted gene expression with an environmental trigger comprising the step of:
  a. fusing a gene for elastin-like polypeptides (ELPs) to a gene for a transcription factor;
  b. cloning the fused gene into an expression system wherein said targeted gene expression is to be regulated;
  c. expressing the ELPs-transcription factor fused gene to produce an ELPs-transcription factor fusion protein; and
  d. initiating an environmental trigger causing the aggregation of ELPs-transcription factor fusion protein whereby said targeted gene expression is regulated.

In some illustrative embodiments, the present invention relates to a method for controlling a targeted gene expression with an environmental trigger, wherein the ELPs is fused to the N-terminus of the transcription factor.

In some illustrative embodiments, the present invention relates to a method for controlling a targeted gene expression with an environmental trigger, wherein the ELPs is fused to the C-terminus of the transcription factor.

In some illustrative embodiments, the present invention relates to a method for controlling a targeted gene expression with an environmental trigger, wherein the environmental trigger is a change of temperature.

In some illustrative embodiments, the present invention relates to a method for controlling a targeted gene expression with an environmental trigger, wherein the environmental trigger is a change of pH value.

In some illustrative embodiments, the present invention relates to a method for controlling a targeted gene expression with an environmental trigger, wherein the environmental trigger is a change of ionic strength.

In some illustrative embodiments, the present invention relates to a method for controlling a targeted gene expression with an environmental trigger, wherein the environmental trigger is a combination of the changes of ionic strength, pH value and/or temperature.

In some illustrative embodiments, the present invention relates to a method for controlling a targeted gene expression with an environmental trigger, wherein said expression system is a bacteria.

In some illustrative embodiments, the present invention relates to a method for controlling a targeted gene expression with an environmental trigger, wherein said bacteria is *E. coli*.

In some illustrative embodiments, the present invention relates to a method for controlling a targeted gene expression with an environmental trigger, wherein said expression system is a yeast.

In some illustrative embodiments, the present invention relates to a method for controlling a targeted gene expression with an environmental trigger, wherein said expression system expresses a natural product or an analogue thereof.

In some illustrative embodiments, the present invention relates to a method for controlling a targeted gene expression with an environmental trigger, wherein said natural product is taxadiene or an analogue thereof.

In some illustrative embodiments, the present invention relates to a product manufactured according to the method for controlling a targeted gene expression with an environmental trigger as disclosed herein.

In some illustrative embodiments, the present invention relates to an expression system comprising a fused gene for a fusion protein of ELPs and a transcription factor, wherein the expression system comprises a targeted gene of which expression is regulated through an environmental trigger.

In some illustrative embodiments, the present invention relates to an expression system comprising a fused gene for a fusion protein of ELPs and a transcription factor, wherein the expression system comprises a targeted gene of which expression is regulated through an environmental trigger, wherein said expression system is a bacteria.

In some illustrative embodiments, the present invention relates to an expression system comprising a fused gene for a fusion protein of ELPs and a transcription factor, wherein the expression system comprises a targeted gene of which expression is regulated through an environmental trigger, wherein said bacteria is *E. coli*.

In some illustrative embodiments, the present invention relates to an expression system comprising a fused gene for a fusion protein of ELPs and a transcription factor, wherein the expression system comprises a targeted gene of which expression is regulated through an environmental trigger, wherein said expression system is a yeast.

In some illustrative embodiments, the present invention relates to an expression system comprising a fused gene for a fusion protein of ELPs and a transcription factor, wherein the expression system comprises a targeted gene of which expression is regulated through an environmental trigger, wherein said expression system expresses a natural product or an analogue thereof.

In some illustrative embodiments, the present invention relates to an expression system comprising a fused gene for a fusion protein of ELPs and a transcription factor, wherein the expression system comprises a targeted gene of which expression is regulated through an environmental trigger, wherein said natural product is taxadiene or an analogue thereof.

In some illustrative embodiments, the present invention relates to an expression system comprising a fused gene for a fusion protein of ELPs and a transcription factor, wherein the expression system comprises a targeted gene of which expression is regulated through an environmental trigger, wherein the sequence of ELPs is fused to the N-terminus of the transcription factor.

In some illustrative embodiments, the present invention relates to an expression system comprising a fused gene for a fusion protein of ELPs and a transcription factor, wherein the expression system comprises a targeted gene of which expression is regulated through an environmental trigger, wherein the sequence of ELPs is fused to the C-terminus of the transcription factor.

In some illustrative embodiments, the present invention relates to an expression system comprising a fused gene for a fusion protein of ELPs and a transcription factor, wherein the expression system comprises a targeted gene of which expression is regulated through an environmental trigger, wherein the environmental trigger is a change of temperature.

In some illustrative embodiments, the present invention relates to an expression system comprising a fused gene for a fusion protein of ELPs and a transcription factor, wherein the expression system comprises a targeted gene of which expression is regulated through an environmental trigger, wherein the environmental trigger is a change of ionic strength.

In some illustrative embodiments, the present invention relates to an expression system comprising a fused gene for a fusion protein of ELPs and a transcription factor, wherein the expression system comprises a targeted gene of which expression is regulated through an environmental trigger, wherein the environmental trigger is a change of pH value.

In some illustrative embodiments, the present invention relates to a product manufactured using an expression system comprising a fused gene for a fusion protein of ELPs and a transcription factor, wherein the expression system comprises a targeted gene of which expression is regulated through an environmental trigger.

In some other illustrative embodiments, the present invention relates to a method for enhancing productivity of a natural product or an analogue thereof comprising the step of:
  a. fusing a gene for elastin-like polypeptides (ELPs) to a gene for a transcription factor;
  b. cloning the fused gene into an expression system wherein expression of gene for said natural product or an analogue thereof is to be regulated;
  c. expressing the ELPs-transcription factor fused gene to produce ELPs-transcription factor fusion protein; and
  d. initiating an environmental trigger causing the aggregation of ELPs-transcription factor fusion protein whereby expression of gene for said natural product or an analogue thereof is regulated.

In some other illustrative embodiments, the present invention relates to a method for enhancing productivity of a natural product or an analogue thereof as disclosed herein, wherein the ELPs is fused to the N-terminus of the transcription factor.

In some other illustrative embodiments, the present invention relates to a method for enhancing productivity of a natural product or an analogue thereof as disclosed herein, wherein the ELPs is fused to the C-terminus of the transcription factor.

In some other illustrative embodiments, the present invention relates to a method for enhancing productivity of a natural product or an analogue thereof as disclosed herein, wherein the environmental trigger is a change of temperature.

In some other illustrative embodiments, the present invention relates to a method for enhancing productivity of a natural product or an analogue thereof as disclosed herein, wherein the environmental trigger is a change of pH value.

In some other illustrative embodiments, the present invention relates to a method for enhancing productivity of a natural product or an analogue thereof as disclosed herein, wherein the environmental trigger is a change of ionic strength.

In some other illustrative embodiments, the present invention relates to a method for enhancing productivity of a natural product or an analogue thereof as disclosed herein, wherein said environmental trigger is a combination of changes of ionic strength, pH value and temperature.

In some other illustrative embodiments, the present invention relates to a method for enhancing productivity of a natural product or an analogue thereof as disclosed herein, wherein said expression system is a bacteria.

In some other illustrative embodiments, the present invention relates to a method for enhancing productivity of a natural product or an analogue thereof as disclosed herein, wherein said bacteria is *E. coli*.

In some other illustrative embodiments, the present invention relates to a method for enhancing productivity of a natural product or an analogue thereof as disclosed herein, wherein said expression system is a yeast.

In some other illustrative embodiments, the present invention relates to a method for enhancing productivity of a natural product or an analogue thereof as disclosed herein, wherein said natural product is taxadiene or an analogue thereof.

In some other illustrative embodiments, the present invention relates to a product manufactured according to the method for enhancing productivity of a natural product or an analogue thereof as disclosed herein, In some other illustrative embodiments, the present invention relates to a method for enhancing productivity of a natural product or an analogue thereof as disclosed herein, wherein ELPs comprise a repeating sequence of (VPGXG)n wherein n is an integral number; X is any amino acid residue except proline, and X may be varied from subunit to subunit.

In some illustrative embodiments, the present invention relates to a method for controlling a targeted gene expression with an environmental trigger, wherein ELPs comprise a repeating sequence of (VPGXG)n wherein n is an integral number; X is any amino acid residue except proline, and X may be varied from subunit to subunit.

In some illustrative embodiments, the present invention relates to an expression system for controlling a targeted gene expression with an environmental trigger, wherein ELPs comprise a repeating sequence of (VPGXG)n wherein n is an integral number; X is any amino acid residue except proline, and X may be varied from subunit to subunit.

In some illustrative embodiments, the present invention relates to a product manufactured biologically according to the method disclosed herein or using an expression system as disclosed in this present patent application.

The stereoselective chemistry of microbes and their ability to convert renewable feedstocks to value-added products have helped to reinvigorate America's bioeconomy with the promise of microbial chemical factories that produce compounds ranging from the industrial solvent 2,3 butanediol to precursors of the antimalarial drug artemisinin (Paddon, C J, et al., *Nature* 2013, 496(7446), 528-532; Alam, M I, et al., *Microbial Applications* 2017, 2, 153-166). Expansion of this currently limited portfolio, however, is hindered by the low yield of many desired products. Despite advances in methods to improve efficiency with genetic circuits that redirect available resources toward product formation, there remains a need for strategies that can dynamically balance product formation and cellular health for superior microbial performance. The invention disclosed herein enables a novel transcriptional gene regulation with the capacity to integrate markers of cellular stress with designated expression profiles for pathway genes to improve production of a natural product or an analogue thereof, such as the anticancer drug precursor taxadiene. This would help transform microbial chemical factory design by introducing a new tool for the design and optimization of novel production pathways, and to broaden the portfolio of feasible products manufactured biologically.

Unlike current available methods, the new class of transcriptional regulators would be modular and universal, as they would have the capacity to recognize the impact of product synthesis on cellular health, and could be tuned for many biomanufacturing processes by manipulating the controller set point via the ELP sequence. Moreover, this technology could be applied to virtually any species by swapping the fused transcription factor with a species-specific transcription factor, thereby greatly simplifying the process of implementing dynamic control. The work disclosed herein will lead to significant increases in the yield of sustainable biomanufacturing processes, including taxadiene production.

This invention focuses on the development of molecular technologies to improve the efficiency of microbial chemical factories, to create orthogonal, transcriptional regulators that dynamically regulate and balance product synthesis with cellular health in microbial chemical factories for significantly improved productivity. As proof of principle, the initial efforts introduce into *E. coli* a series of engineered proteins derived from elastin-like polypeptides (ELPs) to optimize production of taxadiene, a precursor for the potent anticancer drug Taxol (FIG. 1) (Ajikumar P K, et al., *Science* 2010, 330, 70-74). ELPs have the well-documented property of reversible self-assembly in response to changes in temperature, pH, and/or ionic strength at a given critical point encoded in their tunable structure (Zhang, Y, et al., *Biomacromolecules* 2006, 7, 2192-2199: Dreher, M R, et al., *J. Am. Chem. Soc.* 2007, 130, 687-694; MacKay, J A, et al., *Biomacromolecules* 2010, 11, 2873-2879). In our preliminary studies, we have demonstrated that reversible aggregation of ELPs fused to non-native transcription factors can effectively function to control gene expression. By using non-native transcription factors, we preclude possible disruption of native processes and, thus, can target regulation to selected genes via a promoter sequence (Rhodius V A, et al., *Molecular Systems Biology* 2013, 9, 702). As the degree of cellular health controls the intracellular ionic strength and pH, the central idea of this invention is that synthetic regulators can be designed to recognize intracellular indicators of cellular health, and can be precisely programmed to autoregulate expression of targeted pathway genes. These devices would provide potentially unprecedented opportunities to enhance biomanufacturing efficiency and help facilitate the development of a sustainable bioeconomy.

Figure 2:
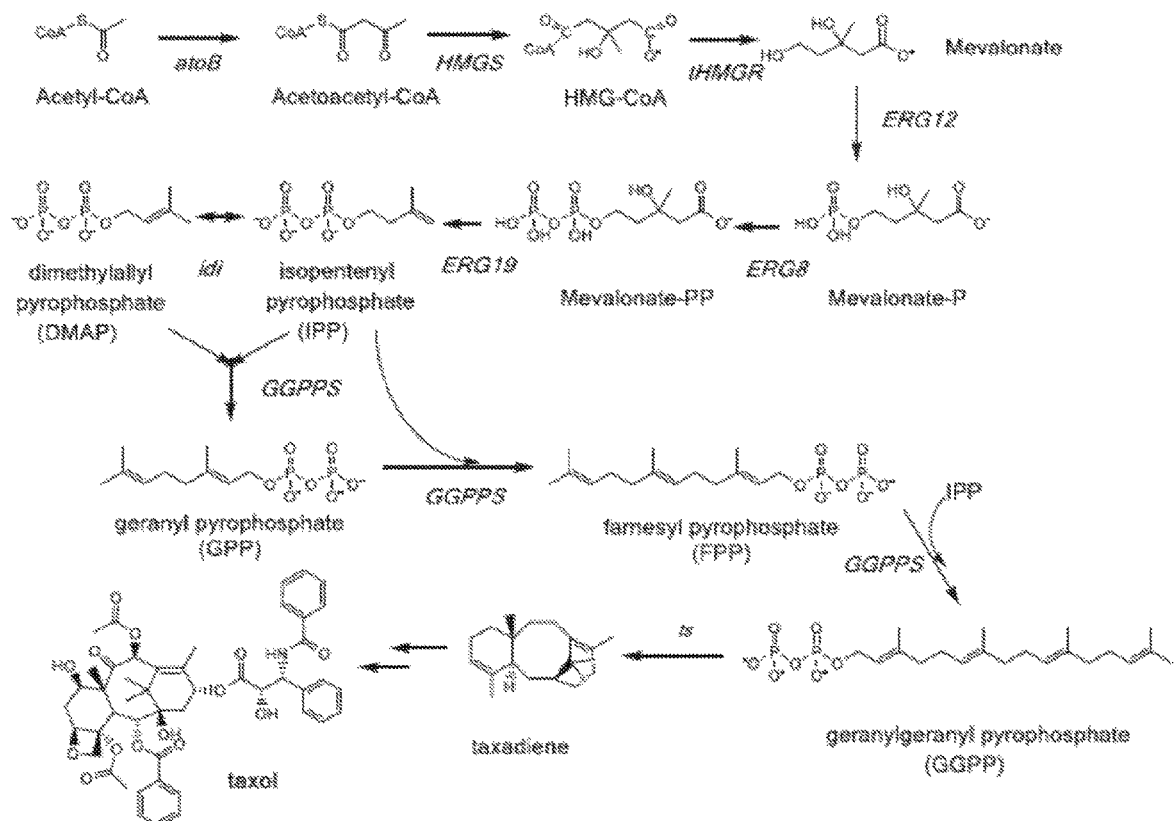
FIG. 2 shows a proposed scheme to taxadiene via the mevalonate isoprenoid pathway (Martin, V J J, et al., *Nat. Biotech.* 2003, 21, 796-802).

Taxol is a derivatized diterpenoid that arises from isoprenoid metabolism, an essential component of lipid metabolism found in all domains of life (FIG. 2). The first committed step of Taxol biosynthesis is the cyclization of the isoprenoid geranylgeranyl diphosphate (GGPP) to taxa-4(5), 11(12) diene (taxadiene) via a taxadiene synthase (Koepp, A E, et al., *J. Biol. Chem.* 1995, 270(15), 8686-8690). Thus, any high titer process for Taxol must produce high yields of the precursor taxadiene. Isoprenoid biosynthesis takes one of two forms: the bacterial methylerythritol-phosphate or the eukaryotic mevalonate pathway. Both pathways have successfully been used to produce taxadiene in *E. coli* and *S. cerevisiae*, respectively (Ajikumar P K, et al., *Science* 2010, 330, 70-74). However, the native pathways are highly regulated due to their essential nature, making them difficult to optimize (Engels, B., et al., *Metabolic Engineering* 2008, 10(3), 201-206). To overcome this challenge, researchers have introduced and optimized expression of the non-native mevalonate pathway in *E. coli* to make g/L titers of other isoprenoid-derived drugs (Martin, V J J, et al., *Nat. Biotech.* 2003, 21, 796-802). Despite this progress, commercial scale titers of Taxol or its precursors have yet to be achieved microbially. Moreover, the overexpression of pathway enzymes to maximize precursor formation may accumulate toxic levels of isopentenyl pyrophosphate (IPP) and farnesyl pyrophosphate (FPP), which reduce yields (Dahl, R H, et al., *Nature Biotechnology* 2013, 31(11), 1039-1046; Martin, V J J, ibid.; Withers, S T., et al., *Applied and Environmental Microbiology* 2007, 73, 6277-6283).

Engineering metabolic negative feedback control to dynamically regulate pathway enzyme expression is a promising approach to overcome pathway intermediate toxicity (Dahl, R H, et al., *Nature Biotechnology* 2013, 31(11), 1039-1046; Zhang, F, et al., *Nature Biotechnology* 2012, 30(4), 354-359). There are unmet needs in the fields of biomanufacturing processes.

Preliminary Studies

To establish the feasibility of using ELPs to control gene expression, we have acquired neutral ELPs from colleagues at UC Riverside and Purdue University consisting of the motif VPGVG at varying lengths fused to either a GST purification tag or a random polypeptide domain (Ge, X, et al., *J. Am. Chem. Soc.* 2009, 131(25), 9094-9099; Liu, J C, et al., *Biomacromolecules* 2004, 5(2), 497-504). Using these samples, we have developed core competencies in the expression, purification and in vitro characterization of ELPs (FIG. 3). ELP phase change is reversible and sharply defined over a narrow programmed range, making them ideal sensors. While ELP phase change displays some hysteresis or dynamic lag in its response, the time scale over which this is observed (1 min) is much shorter than typical biological processes (~10 min) and unlikely to have a significant impact on the controllability of in vivo performance. As these ELP had no acidic or basic residues to evaluate pH sensitivity, we tested the ability of ELPs to respond in vitro to the presence of environmental signals that could interact with ELP aggregation behavior (as pH would). ELPs were able to interact with mildly hydrophobic butanol to increase the transition temperature in a dose dependent manner. Under isothermal conditions (such as during cell culture), butanol would be able to independently trigger ELP phase change by increasing the transition temperature, ultimately dissolving ELP aggregates once the transition temperature exceeded the culture temperature. Thus, these preliminary data support the feasibility of ELP as a programmable sensor element to recognize environmental triggers in solution.

Figure 4A:
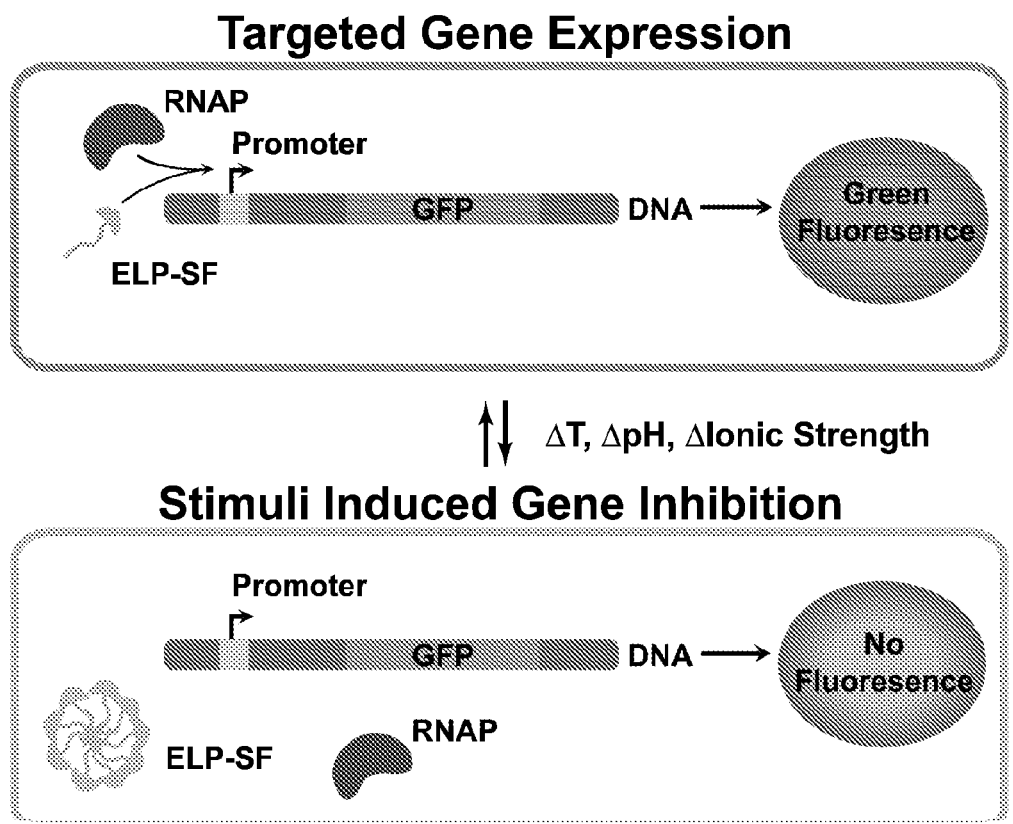
FIG. 4A shows a proposed mechanism of action of a constructed system of ELP-sigma factor fusions control gene expression in response to stimuli.
Figure 4B:
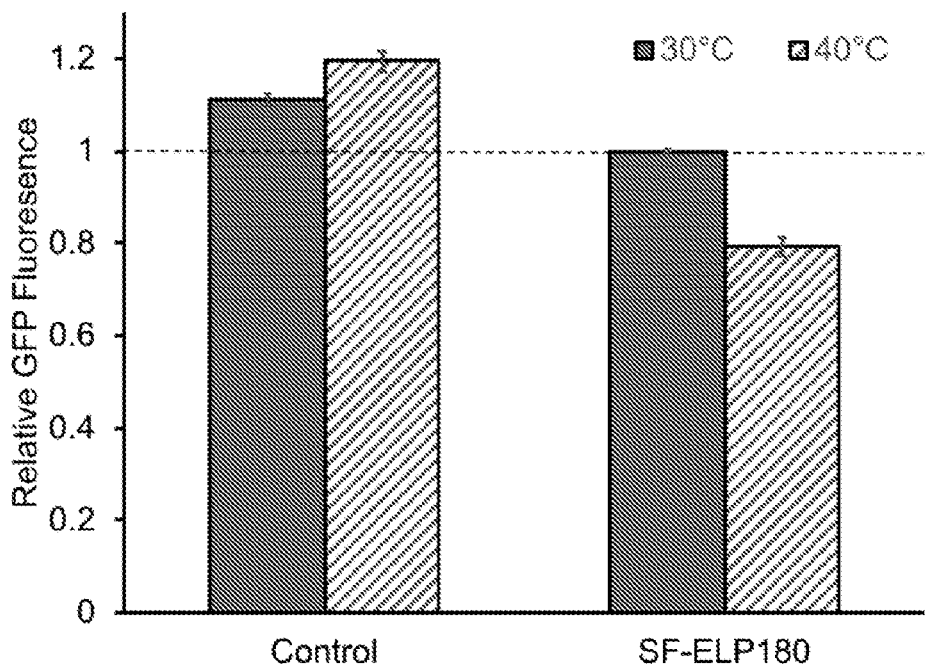
FIG. 4B depicts relative normalized green fluorescence of *E. coli* MG1655 at 30° C. and 40° C. expressing GFP from $P_{ECF20}$ regulated by sigma factor ECF20. A control (ECF20 sigma factor) and ELP-SF (GST-ELP128-sigma factor fusion) were expressed from a T7 promoter using T7 RNA polymerase induced from vector pN565, while GFP was expressed from pVRb (Rhodius, V A, et al., *Molecular Systems Biology* 2013, 9, 702. Doi:10.1038/msb.2013.58).

We then examined the ability of ELPs to regulate in vivo gene expression through orthogonal ELP-sigma factor fusions (FIG. 4). We fused a bacterial transcription factor, ECF20, to the C-terminus of GST-ELP128 and assessed the ability of the fusion to a) drive gene expression of green fluorescent protein (GFP) from a promoter activated by ECF20 and, b) be regulated by ELP aggregation. ECF20 and its corresponding promoter are non-native to $E.$ $coli$ and do not interact with its promoters nor sigma factors, respectively (Rhodius, V A, et al., $Mol.$ $Systems$ $Biology$ 2013, 9, 702). Thus, any fluorescence that is observed is due solely to the activity of our engineered ELP-sigma factor fusion. We grew $E.$ $coli$ cultures containing the ELP construct and GFP at a low and high temperature to stimulate ELP aggregation or dissolution before measuring the steady state fluorescence of the cultures. ELP-sigma factor fusions displayed comparable fluorescence to that of sigma factor controls at 30° C. However, at the elevated temperature of 40° C., the ELP-sigma factor construct displayed a 20% reduction in fluorescence ($p=0.01$) while the control did not display a statistically significant change in fluorescence ($p=0.06$). This experiment demonstrates an ability of ELP-transcription factor fusions to regulate gene expression in a stimuli-dependent manner. This invention disclosed herein: 1) creates a library of ELP sensor-regulators and characterizing their gene regulation properties in multiple species, 2) develops a production pathway test platform and identifying conditions in a metabolic pathway under which such ELP regulators might be useful, and 3) evaluates the dynamic properties of ELP regulators and assesses their ability to optimize biomanufacturing of taxadiene in a bacteria and a yeast expression system.

Quantify the Transcriptional Response of Synthetic ELP-Transcription Factor Fusions We hypothesize that engineered ELP-transcription factor fusions regulate genes over a characteristic range of expression levels and response times determined by regulator composition; and ELP-based regulators can be implemented in different species with appropriate transcription factors. While our preliminary studies demonstrate a capacity for ELP-transcription factor fusions to reproducibly regulate gene expression in response to environmental stimuli, the full potential of this technology remains to be determined. We further evaluate this potential expression method in both $E.$ $coli$ and $S.$ $cerevisiae$, a bacteria and a yeast expression system, respectively. The approach is to build a library of ELPs varying in length and composition to enable reversible aggregation under increased temperatures, and changes in pH, and fuse them to species-specific transcription factors to moderate gene expression. The phase change properties of these constructs are characterized in vitro via a visible spectroscopy, while the in vivo ability to control a gene expression is evaluated with a reporter GFP gene under the control of a promoter that recognizes the fused transcription factor.

Figure 5A:
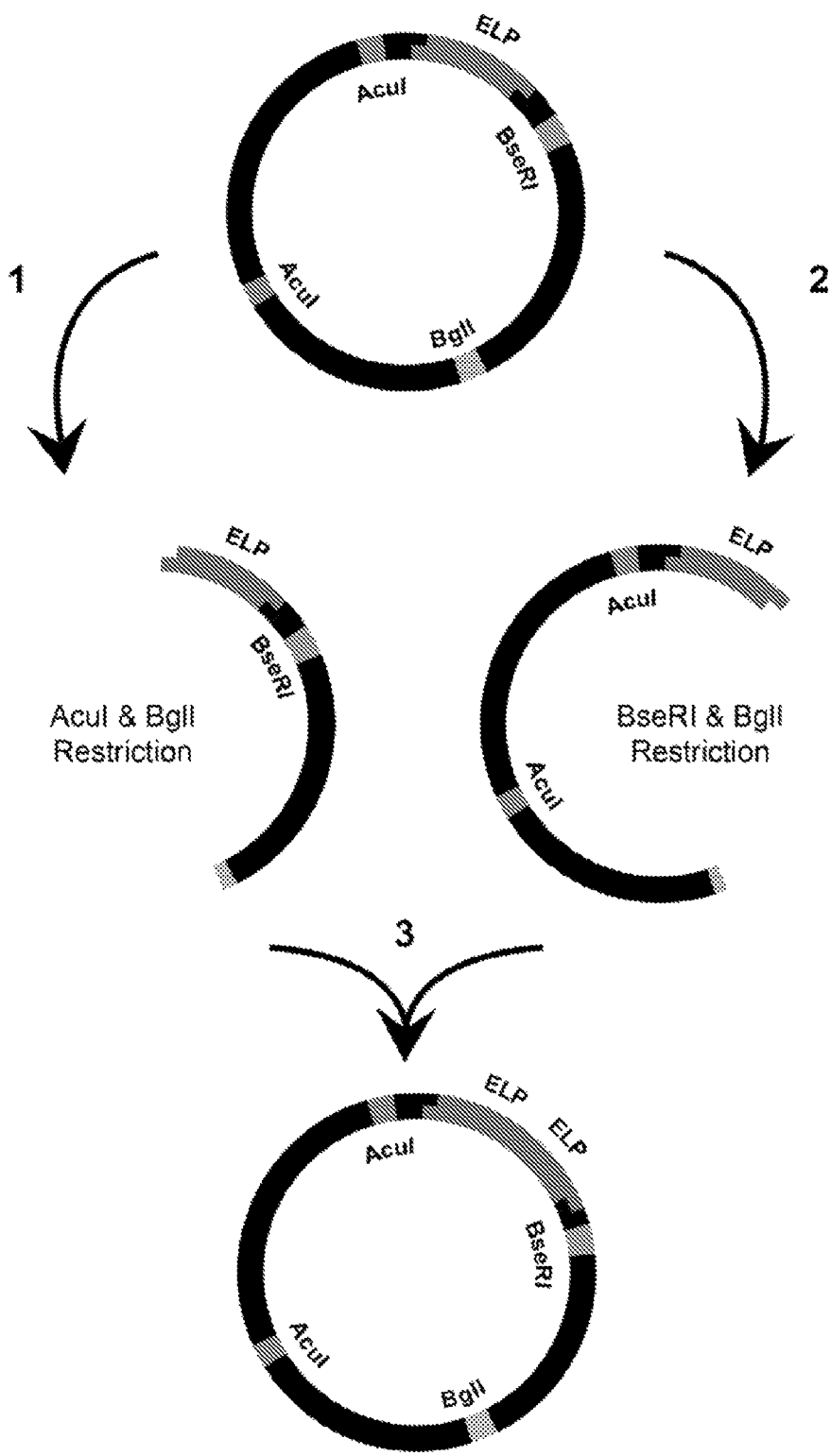
FIG. 5A shows the construct of expression vector. In Pre-RDL, the parent vector is digested with (1) AcuI and BglII, and (2) BseRI and BglII. ELP-containing DNA fragments are purified and (3) ligated together to reconstruct a functional plasmid, increasing the ELP length.

Establish a Library of ELPs that Aggregate Under Diverse Environmental Conditions As ELPs consist of a repeating amino acid and nucleic acid sequence, creating a library of new constructs with common methods such as PCR or DNA synthesis are infeasible (Hommelsheim, C M, et al., $Scientific$ $Reports$ 2014, 4: SREP05052). Thus, the approach here is to build the library in pET28 using plasmid reconstruction via recursive directional ligation (PRe-RDL), which has been developed to create difficult constructs such as ELPs (FIG. 5A) (McDaniel, J R, et al., $Biomacromolecules$ 2010, 11(4), 944-952). First, we generate a linker sequence via primer annealing that contains the Type IIS restriction sites BseRI and AcuI, and integrate it in the multiple cloning site of pET28 via a conventional restriction digest and ligation (FIG. 5B and FIG. 5C). Type IIS restriction sites are recognized by restriction enzymes that cleave at a set distance from the recognition site, allowing us to define the sequence at the junctions of subsequent ligation reactions using these sites (Casini, A, et al., $Nature$ $Reviews$ $Molecular$ $Cell$ $Biology$ 2015, 16(9), 568-576). We then generate a base 25-mer ELP subunit [$(VPGXG)_5$] via primer annealing, and integrate the product between the AcuI and BseRI sites.

As disclosed herein, ELPs comprise a repeating sequence of $(VPGXG)n$ wherein n is an integral number; X is any amino acid residue except proline, and X may be varied from subunit to subunit. For an acidic ELP, X is Val/Ile/Glu in a ratio of 1:3:1. For a basic ELP, X is Val/His/Gly/Ala in a ratio of 1:2:1:1. For a neutral ELP, X is Val.

Figure 3A:
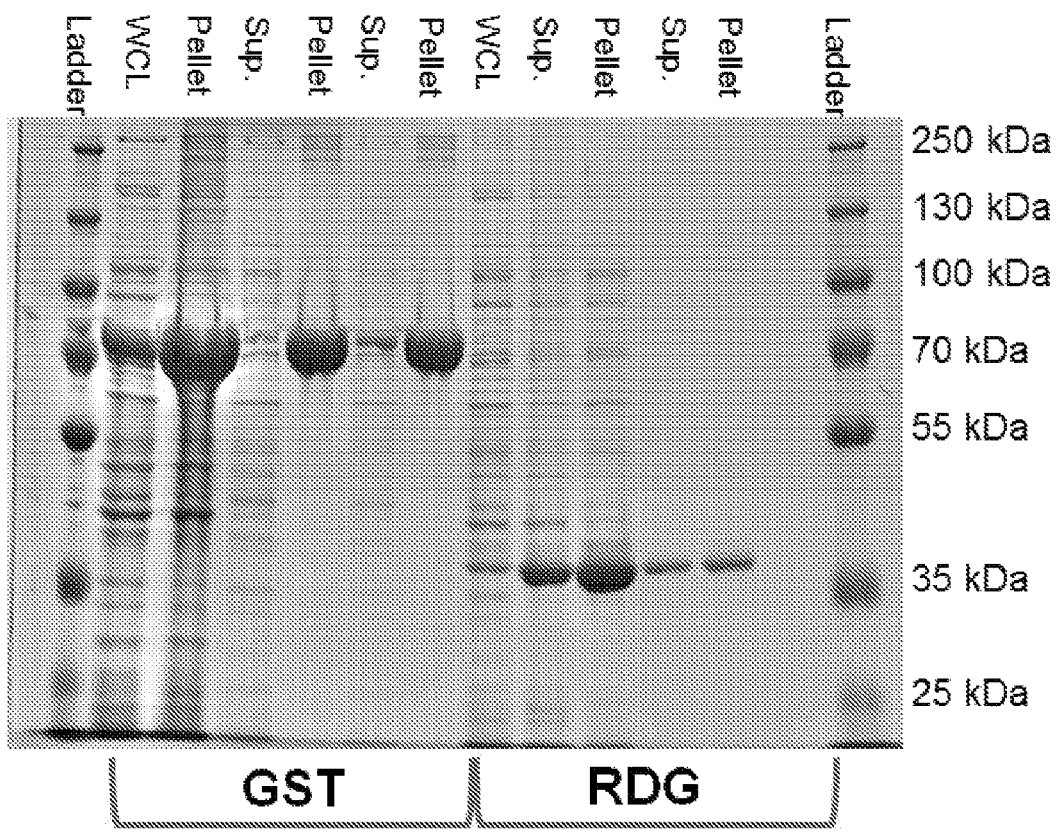
FIG. 3A shows that GST-ELP128 (70 kDa) and RDG-ELP 64 (40 kDa) are readily expressed in BL21(DE3). ELP is purified by sonicating and pelleting cell debris before aggregating ELPs in the lysate at 40° C. (Pellet) and washing 3× with TN buffer (10 mM Tris, 100 mM NaCl, pH8).
Figure 3B:
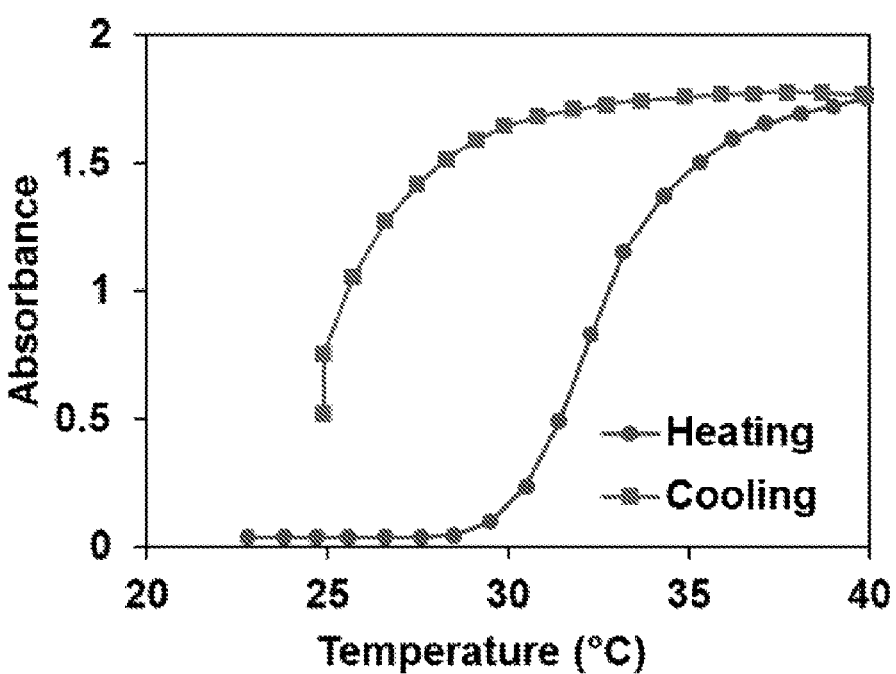
FIG. 3B shows that purified GST-ELP128 displays a sharp phase transition with increasing temperature to form a turbid solution. Phase change monitored at 600 nm while increasing temperature by 1° C./min.
Figure 3C:
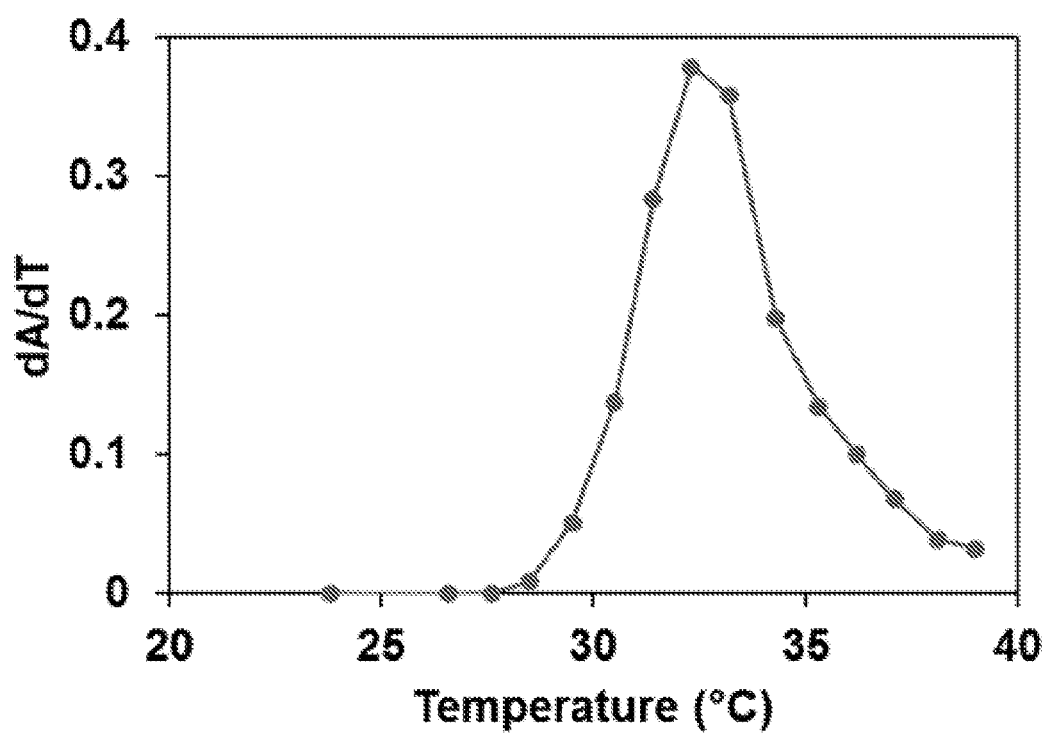
FIG. 3C shows that the transition temperature of GST-ELP128 may be determined from the peak change in absorbance per unit temperature (dA/dT).
Figure 3D:
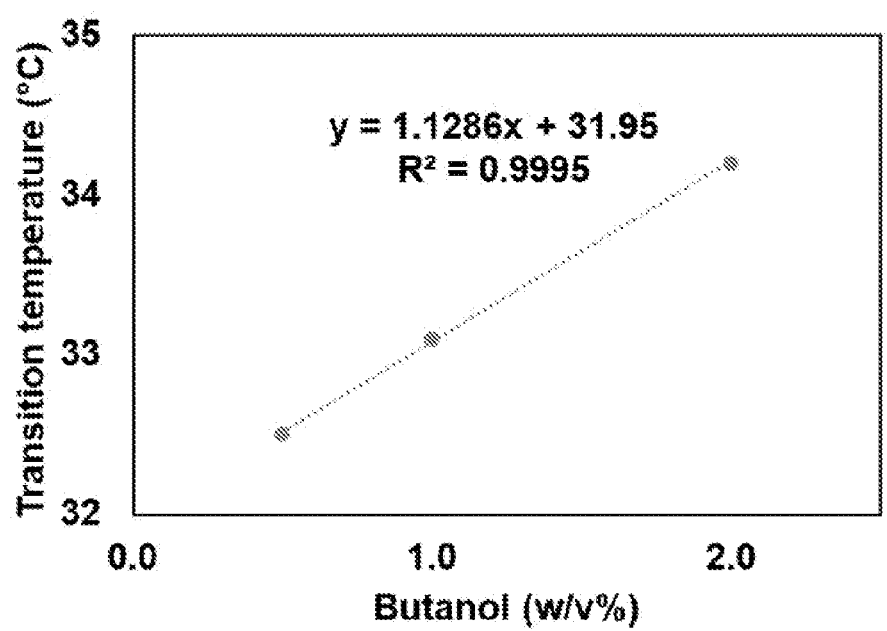
FIG. 3D shows that ELPs may be used as biological sensors as small molecules such as butanol can disturb GST-ELP128 aggregation raising the transition temperature in a dose dependent manner.

After incorporation, we cut with either AcuI or BseRI, and a third site found in the vector backbone, BglII, to ligate together multiple 25-mer subunits. This can be repeated in an iterative fashion to double the ELP length in a single round, or add a smaller defined subunit (e.g. a single 25-mer), and rapidly generate ELPs that may phase change under physiologically relevant conditions of 20-40° C., 0.85% NaCl (~0.15 M), and pH=6-8 as measured in vitro with visible spectroscopy (FIG. 3B). By using these Type IIS sites, we can create ELP constructs of arbitrary length that remain undisrupted by fusion 'scar' sequences typical of traditional restriction enzymes. In the initial constructs, we design acidic ELPs that aggregate with decreasing pH, basic ELPs that aggregate with increasing pH, and neutral ELPs that are insensitive to pH (FIG. 5C). Guest residues are varied in the acidic and basic ELPs as indicated to tune the free energy of the system and allow for phase change at physiologically relevant temperatures using minimal sequence length (MacKay, J A, et al., $Biomacromolecules$ 2010, 11(11), 2873-2879). We then measure in vitro the transition pH and transition temperatures of constructs purified as described in FIG. 3A by monitoring increases in absorbance with changes in stimuli. At the conclusion of these studies we expect to have constructed and identified at least 3 acidic, 3 basic, and 3 neutral ELPs that phase change under physiological conditions and will serve as the sensor element of our controllers.

Figure 6:
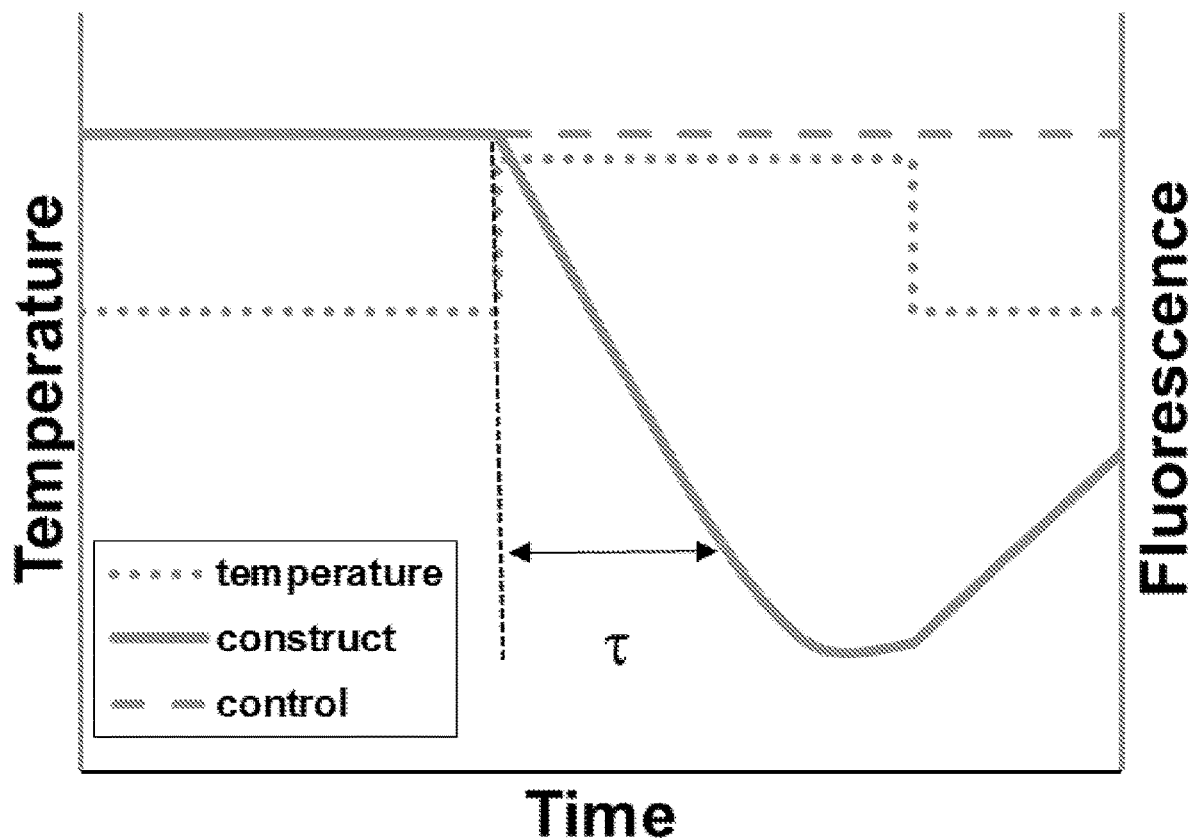
FIG. 6 shows anticipated results from a dynamic control experiment with stepwise control of temperature.

Create Transcriptional Circuits Incorporating ELP as a Sensor and Characterize their Performance The approach is the similar to the one pursued in the preliminary studies. As pH responsive ELPs will also respond to elevated temperatures, we use a common experimental framework of temperature change to initially evaluate transcriptional circuit performance. Briefly, we fuse ELP to various transcription factors on the C-terminus with a flexible 5xGly linker and test the ability of the construct to drive expression of a reporter green fluorescence protein (GFP) gene under the control of the corresponding promoter. We then assess the ability of the construct to control expression under a range of temperatures (25-40° C.) by culturing cells at different growth temperatures and measuring the fluorescence in mid-log phase via a plate reader to derive a relationship between temperature (stimuli-induced control) and gene expression. As a negative control, we measure the fluorescence from cultures where the reporter gene is driven directly by transcription factor. Feedback controllers must respond to positive and negative deviations beyond their set point reversibly and quickly. Thus, we need to evaluate the reversibility and response time of any ELP-mediated regulation by varying temperature in a stepwise fashion and measuring the time until fluorescence achieves ~63.2% steady state to calculate a characteristic time constant (t, FIG. 6). This is repeated for increases and decreases in temperature to assess the suitability of a given ELP-transcription factor construct as a regulator.

To test regulation in E. coli, we initially fuse ELP to either an orthogonal sigma factor, ECF20 (Rhodius, V A, et al., Mol. Systems Biol. 2013, 9, 702), or TetR (Guzman, L M, et al., J. Bacteriol. 1995, 177, 4121-4130) to create opposing control modalities. ECF20 is a transcriptional activator, which should lead to decreases in gene expression when sequestered within an ELP aggregate. In contrast, TetR is a transcriptional repressor, which should lead to increases in gene expression when aggregated with ELP. We also test the ability of ELP transcriptional regulators to function in species other than E. coli. We fuse ELP to tTA (tetR-VP16/Tet-Off) and express it from the inducible yeast episomal vector YEp351 to assess the ability of ELP-tTA and ELP-TetR (Tet-On) to regulate expression of eGFP from the TetR-CYC1 promoter in S. cerevisiae as described above (Gari, E, et al., Yeast 1997, 13(9), 837-848; Hill, J E, et al., Yeast (Chichester, England) 1986, 2(3), 163-167). Finally, we evaluate the ability of ELP-transcription factor constructs to form multiplexable circuits with independent triggers without cross-talk. Two ELP-transcription factor constructs from E. coli using two different orthogonal sigma factors fused to separate ELPs with distinct transition temperatures (e.g. 30 and 37° C.) is used to independently drive the expression of GFP and RFP at different temperatures. This performance is compared to that of the constructs in isolation to identify any potential for cross-talk. At the conclusion of these studies, we expect to have measured the potential response of ELP-transcription factor regulators, and established the suitability of individual designs to regulate gene expression in a feedback controller, and in more complex multiplexed gene circuits.

Accomplishment of this study is expected to result in several ELP-transcription factor constructs that may be used to control gene expression as new temperature responsive and pH responsive regulators at distinct set points encoded in their structure. We anticipate measuring in vitro the triggers for these new devices and their in vivo dynamic responses to form a library that allow users to tune gene expression within a range of values by selecting the appropriate transcriptional regulator. It is expected that these tunable transcriptional regulators phase change under physiological conditions in multiple species with minimal cross-talk, enabling their use as negative feedback controllers in multiplexed gene circuits that resist deviations from cellular homeostasis.

Potential Problems and Alternative Approaches.

Although different ELP-transcription factor constructs may not have wide dynamic ranges as transcriptional regulators, given our preliminary data it is unlikely that all of our engineered constructs will fail to regulate gene expression. However, it may be possible that initial designs are unable to perform as designed. For example, the ability to drive expression may be compromised by an N or C terminal fusion of the transcription factor to ELP. Thus, we may need to explore fusions at the opposite end of the ELP protein, or vary the linker length to reduce steric interference between the transcription factor and ELP. Similarly, some transcription factors may not tolerate fusion at all at which time we would consider any of the other known transcriptional regulators (e.g. LacI or AraC in E. coli, and Gal4 in yeast. See: Traven, A, et al., EMBO Reports 2006, 7(5), 496-499; Lutz, R, et al., Nucl. Acids Res. 1997, 25, 1203-1210; Andersen J B, et al., Applied and Environmental Microbiology 1998, 64(6), 2240-2246). Another potential problem could be the dynamic performance of constructed gene circuits. While ELP phase change, and thus transcriptional regulation, are rapid (minutes), the dynamics of such a gene circuit would be dictated by the stability of the proteins being expressed such as GFP. Thus, it may be difficult to observe or accurately estimate the dynamic response. To address this, we are currently building a dynamic model of potential gene circuits incorporating ELP based on mass action kinetics, empirical modeling of experimental phase change data, and mass balances to identify the rate limiting steps. Should our model or experiments indicate an issue with regulator dynamics, we could destabilize problem proteins identified in the model as needed with degradation tags such as LVA (Meier, S D, et al., J. Neuroscience Methods 2006, 155(2), 251-259).

Correlate Level of Taxadiene Production with Markers of Cellular Health in Engineered E. coli Based on reports that an acid-stress promoter has been successfully used to regulate the isoprenoid pathway, production of taxadiene via toxic isoprenoid intermediates in E. coli directly alters intracellular pH, $K^+$, and/or $Na^+$ to impact cellular health (Dahl, R H, et al., Nature Biotechnology 2012, 31(11), 1039-1046).

Implement and Optimize the Mevalonate Pathway for the Production of the Taxadiene Precursors.

The mevalonate pathway for biosynthesis of taxadiene precursors is non-native to E. coli and must be heterologously introduced and expressed (see FIG. 2). Subcomponents of these pathways from organisms such as S. cerevisiae, S. pneumoniae, and E. faecelis, have been optimized for expression in E. coli to convert acetoacetyl-CoA to DMAP, but there has been, to date, no systematic optimization of individual genes described in the literature. Thus, our approach to addressing this task is to combinatorially assemble the pathway genes under the control of a library of mutant T7 promoters using the ePathOptimize system (Jones, J A, et al., Scientific Reports 2015, 5: SREP11301). Using this plasmid system, we can optimize production of taxadiene precursors by modulating the expression of each gene of the pathway individually.

Briefly, we clone the 7 mevalonate genes from previously described plasmids pMevT and pMBIS (Martin, V J J, et al., Nat. Biotech. 2003, 21, 796-802) and the geranylgeranyl pyrophosphate synthase (GGPPS) gene from p20TrcGT (Ajikumar, P K, et al., Science 2010, 330, 70-74) into the ePathBrick vector pETM6. Next, the genes are sub-cloned into a library of pETM6 vectors containing one inducible T7 promoter from a library of 5 mutants with varying expression strengths, or a weak constitutive promoter from the vector pXylA (Pitera, D J, et al., Metab. Eng. 2007, 9, 193-207). From these libraries we can use sub-cloning to combinatorially build randomized libraries of the complete pathway. In parallel, we examine the effect of metabolic burden placed on the cell by discretizing the pathway into modules that reduce the number of biochemical steps that are realized in a single cell. Each module is independently expressed by an *E. coli* strain. The various modules are then combined in a single co-culture of different *E. coli* that is simultaneously expressed to produce intermediates that freely diffuse from cell to cell and react to form the desired product. The first module (Module 1) contains the genes to convert acetyl-CoA to free diffusing mevalonate (Jones, J A, et al. 2015; Wang, C-W, et al., *Biotechnology and Bioengineering* 1999, 62(2), 235-241). The second module (Module 2) converts mevalonate to geranylgeranyl diphosphate (GGPP). As GGPP is not freely diffusible, the taxadiene synthase is expressed from a second plasmid in strains containing Module 2 (Xue, D, et al., *Applied Microbiology and Biotechnology* 2015, 99(14), 5907-5915). In this co-culture system, each module is optimized individually, independent of the other module, and then the highest-producing strains from each module is inoculated together in varying ratios to determine the optimum for production. For the first module (3 genes), this results in a total of 216 constructs (6 different promoters→$6^3$). The second module (5 genes) consists of 7,776 possible constructs ($6^5$). Due to the high number of possible combinations, a high-throughput screen will be necessary to determine high-production strains.

Figure 7:
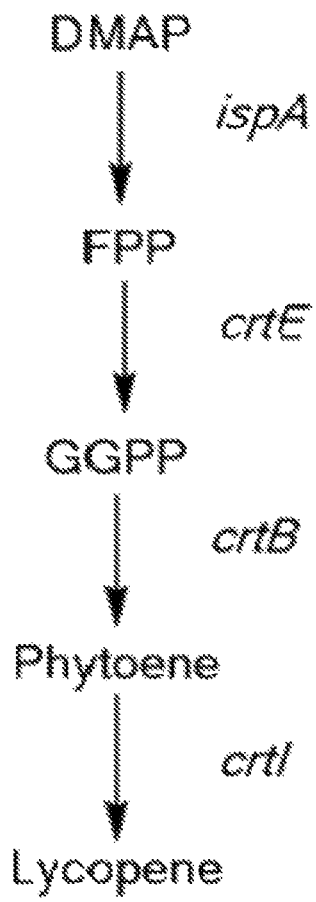
FIG. 7 shows the native *E. coli* genes (ispA) and the crt operon from pAC-Lyc convert DMAP to the bright red lycopene.

Production of lycopene, a carotenoid and red pigment, utilizes many of the same intermediates as the mevalonate pathway including FPP and GGPP. Previous work in the literature has demonstrated that increased production of mevalonate led to an increase in carotenoid production in *Bacillus*, and a similar biosensor system has been used in yeast to determine genes with roles in isoprenoid production (Xue, D., et al., ibid.; Ozaydin, B, et al., *Metabolic Engineering* 2013, 15, 174-183). We use the lycopene pathway expressed from the previously described vector pAC-LYC, consisting of the operon crtEIB, to convert isoprenoid intermediates to lycopene (FIG. 7) (Cunningham, F X, et al., *The Plant Cell Online* 1994, 6(8), 1107-1121). The basis of our use of this pathway as a biosensor is that increased intracellular concentrations of the intermediates mevalonate or GGPP result in higher lycopene production, or darker red colonies, which can be measured by visible spectroscopy in high throughput. Using this colorimetric biosensor screen we identify constructs resulting in low- to high-producing strains. DNA sequencing is used to determine which promoters in our library correlate with high or low levels of production. Thus, after screening with lycopene, we are able to grow high-producing strains in pure culture to quantify terpenoid production using analytic HPLC and GCMS methods analysis. At the conclusion of these studies, we expect to have implemented the mevalonate pathway in *E. coli* and to have generated a set of strains that produce mevalonate, GGPP and taxadiene at varying levels. These strains are then used to develop a modular co-culture system capable of producing high-value terpenoid products, and will also be used to study the impact on the intracellular environment of variably-producing strains.

Characterize the Intracellular pH, $K^+$ and $Na^+$ Levels in IPP/FPP/GGPP Producing Cells.

The study here is to coexpress, or introduce, commercially available fluorescent probes that are confirmed to be sensitive to pH, $K^+$, or $Na^+$ levels as a noninvasive, real-time method to evaluate the impact of mevalonate production on cellular health. There are several engineered mutants of fluorescent proteins which display pH sensitivity and may be used to noninvasively measure intracellular pH (Arosio, D, et al., *Nature Methods* 2010, 7(7), 516-518: Orij, R, et al., *Microbiology* 2009, 155(1), 268-278; Kneen, M, et al., *Biophysical J.* 1998, 74(3), 1591-1599; Mahon, M J, et al., *Advances in Bioscience and Biotechnology (Print)* 2011, 2(3), 132-137; Tantama, M., et al., *J. Am. Chem. Soc.* 2011, 133(26), 10034-10037). Here, we use the RFP mutant pHRED developed by collaborators, which is a ratiometric pH sensitive marker that can be excited at either 440 nm or 585 nm to emit at 610 nm. However, as the pH increases, excitation at 585 nm decreases while excitation at 440 nm increases. Thus, we are able to accurately correlate the intracellular pH with the ratio of fluorescence after excitation at 440 nm and 585 nm to noninvasively measure intracellular pH. More importantly, by measuring fluorescence ratiometrically in this manner, the pHRED probe serves as its own internal control that reduces possible measurement errors due to variations in levels of protein expression. For these experiments, we first express pHRED alone in *E. coli* BL21 (DE3) using a weak constitutive promoter (J2313, Anderson promoter library, parts.i-gem.org). We then incubate these cells in buffer solutions ranging from pH 6-8 with 20 mM sodium benzoate, an ionophore that permeabilizes the membrane thereby allowing the intracellular pH to equilibrate with the buffer solution (Wilks, J C, et al., *J. Bacteriol.* 2007, 189(15), 5601-5607). After sufficient equilibration time, we measure the fluorescence ratio of pHRED to generate a calibration curve of pH with fluorescence.

We then co-express pHRED with the mevalonate pathway encoding plasmids described above in shake-flask cultures and regularly sample the culture to track fluorescence with mevalonate, and taxadiene production. In parallel experiments, we also measure changes in intracellular $K^+$ and $Na^+$ levels with either the $K^+$-selective benzofuran isopthalate fluorophore (PBFI; Ex 380 nm/Em 500 nm) (Meuwis, K. et al., *Biophysical J.* 1995, 68(6), 2469-2473; Yoon, S.-H., et al., *J. Biotechnol.* 2009, 140(3-4), 218-226), or the $Na^+$ selective fluorophore CoroNa Green $Na^+$ (Ex 492 nm/Em 516 nm) (Chen, Z. et al., *J. Biol. Chem.* 2002, 277 (27), 24653-24658). These ion selective fluorophores demonstrate strong increases in fluorescence in the presence of their selected ion with weaker dependence on pH. To correlate ion concentration with fluorescence, we first take small samples of control *E. coli* BL21 (DE3) and incubate the cells with dye to load them. We then incubate the cells in increasing concentrations of KCl solution and nigericin to equilibrate potassium concentrations (Graven, S N, et al., *PNAS USA* 1966, 56(2), 654-658), or increasing concentrations of NaCl and gramicidin to equilibrate sodium concentrations between the buffer and the cell cytoplasm (Kelkar, D A, et al., *Biochimica et Biophysica Act (BBA)—Biomembranes* 2007, 1768(9), 2011-2025). The fluorescence of these treated cells are then used to generate calibration curves for buffer ion concentration at various pH. Once we have created these curves, we express the plasmid-based mevalonate pathway in a shake flask culture, and periodically sample the cells to load them with dye and assay potassium and sodium concentrations. Completion of these studies is expected to allow us to noninvasively quantify how intracellular pH, $K^+$ and/or $Na^+$ are affected by mevalonate production.

Accomplishment of this study results in the quantification of the impact of mevalonate and taxadiene production on intracellular pH, $K^+$ and/or $Na^+$, and establishes a high producing strain for taxadiene precursors. We anticipate being able to document a strong correlation with cellular health (or deviation from cellular homeostasis) and production as influenced by high, medium, and low production plasmids. That, in turn, help to establish key metabolic set points for those parameters that must be maintained by the proposed transcriptional regulators.

Potential Problems and Alternative Approaches. While the extent to which taxadiene production impacts intracellular levels of $K^+$ or $Na^+$ is currently not known, there is strong evidence in the literature to suggest an effect on intracellular pH (Dahl, R H, et al., *Nature Biotechnology* 2013, 31(11), 1039-1046). Notwithstanding this, however, the magnitude of this deviation may prove to be too small to measure accurately. In such a case, we would shift our attention to other fluorometric pH sensors such as phluorin (Mahon, M J, et al., *Advances in Bioscience and Biotechnology*, 2011, 2(3), 132-137) or more sensitive methods such as NMR to measure pH changes (Cohen, J S, et al., *Magnetic Resonance in Medicine* 2004, 51(5), 900-903). While this could be less convenient than the proposed primary approach, it is nevertheless still feasible. An alternate approach could also exploit the fact that intracellular pH is primarily maintained through a proton pump that extrudes protons to establish a membrane gradient that can be used to generate energy. Decreases in intracellular pH are accompanied by increases in pumping activity and increased membrane potential (Zilberstein, D. et al., *J. Bacteriol.* 1984, 158(1), 246-252). Thus, we could, if necessary, measure this membrane potential using more invasive methods in order to assay the intracellular pH. Other potential problems could include difficulties in identifying high, medium, and low mevalonate producing strains using the proposed combinatorial approach. However, the mevalonate pathway has been studied and optimized in *E. coli* for over 10 years with published implementations attaining a range of production titers. From this collected body of work, we could identify and request plasmids from the corresponding authors with production titers at the desired levels to serve as viable alternatives.

Identify Synthetic ELP-Transcription Factor Fusions that Improve Taxadiene Production by Introducing Negative Feedback Regulation of Key Genes Engineered ELP-transcription factor fusions are able to selectively recognize changes in homeostatic conditions (e.g. pH), and regulate expression of metabolic genes that control flux through the isoprenoid pathway to reduce toxic intermediate accumulation and promote taxadiene production. Here we measure in vivo phase change of the ELP library via fluorescent microscopy with ELP-GFP fusion, and identify appropriately tuned ELP-transcription factor fusions and characterize the impact of ELP based negative feedback on yields of taxadiene While dynamic stress response promoters have been identified that have the capacity to regulate the production of isoprenoids via the mevalonate pathway (Dahl, R H, et al, 2013), the response of this system may well be suboptimal, as it was evolved in a context far removed from biomanufacturing. Our objective in this study is to identify tunable ELP-transcription factor fusions that can detect and respond to changes in the intracellular environment to optimize taxadiene production. This study is to characterize the in vivo phase transition properties of a library of ELP-transcription factor constructs to identify appropriate controllers that are then used to control the flux of toxic IPP (Martin, V J J, et al, *Nat. Biotech.* 2003, 21, 796-802). We have established that ELPs are environmentally responsive phase changing proteins that can function to sequester fused transcription factors to control gene expression, thereby introducing much needed feedback control to maintain toxic intracellular intermediates at low levels, and improve cellular health and production yields. At the conclusion of this study, we would have improved the yield of the isoprenoid pathway through ELP-transcription factor feedback controllers and other methods to optimize the production of taxadiene and other value-added chemicals.

Measure the in vivo phase transition properties of our ELP library. As the inverse phase change behavior of ELPs is dependent on ionic strength, pH, ELP concentration, and temperature, which are all relatively fixed in the cell, we need to establish how engineered ELP-transcriptional controllers will behave in a cellular context. Thus, it is necessary to characterize the phase transition properties of ELP under different expression strengths to identify the optimal design for a controller that would be triggered at metabolic set points identified to correlate with poor cellular health. Our approach is to visualize this in vivo transition similar to that of Ge et al (Ge, X, et al., *J. Am. Chem. Soc.* 2009, 131(25), 9094-9099). Briefly, we fuse the members of our ELP library with C-terminal GFP separated by a 5×Gly linker, and express the library in *E. coli* from a plasmid with either a strong, medium, or weak constitutive promoter from the Anderson collection (J23101, J23111, J23116; relative strengths 0.70, 0.58, 0.15 as reported in the iGEM Registry, parts.igem.org). ELP-GFP fusions are visible under microscopy as diffuse fluorescence throughout the cell. However, when the inverse phase change is triggered, the fluorescence migrates to the poles of the cell forming a separate aqueous phase. We grow cells expressing this fusion protein under a fluorescent confocal microscope and then vary temperature or intracellular pH using an ionophore and buffer to trigger the phase change. The process of aggregation is monitored via microscopy in order to identify the metabolic set points, or conditions, for a given construct at a given expression level that triggers aggregation. These data are used to construct an empirical model for how ELP concentration or expression affects phase change in vivo by comparing total fluorescence per cell (expression) to the transition trigger for different constructs. At the conclusion of these studies, we expect to have evaluated the in vivo phase change triggers of aggregation and their dependence on ELP expression strength in order to inform selection of appropriate constructs that will function as negative feedback controllers to optimize taxadiene production.

Characterize the impact of ELP based negative feedback on ERG19 and GGPPS expression on yields of taxadiene. Toxicity in the production of taxadiene and other isoprenoids is believed to arise from accumulation of IPP (Martin, V J J, et al., *Nat. Biotech.* 2003, 21, 796-802). This toxicity is believed to increase intracellular pH, leading to cell death and poor production yields. Thus, negative feedback regulators that recognize the impact of IPP accumulation, namely shifts in intracellular pH, to regulate the flux of IPP may lead to increased cell viability and improved productivity. We examine two control architectures for a potential negative feedback controller based on our designed ELP-transcription factor regulators. In the first architecture, the ability of positive regulation that pulls flux away from IPP under cell stress (increasing pH) by increasing GGPPS synthesis is evaluated. Here, we use an acidic ELP-ECF20 controller tuned to dissolve with increased intracellular pH to activate gene expression of GGPPS driven by $P_{ECF20}$. Similarly, we examine basic ELP-TetR that aggregates under increasing pH to derepress GGPPS driven by $P_{tet}$. In parallel, the negative control architectures that reduce the expression of ERG19 to reduce IPP accumulation are examined. Here, we use a basic ELP-ECF20 fusion that aggregates with increased pH to deactivate expression of ERG19 driven by $P_{ECF20}$. And again, we test an acidic ELP-TetR used to drive ERG19 from P$_{tet}$ where increased pH increases the amount of free TetR, thereby increasing TetR repression of ERG19. While these studies may be empirically undertaken, research results from previous research tasks are used to guide the design and construction of these constructs. We implement designs tuned to respond to deviations beyond nominal intracellular pH in E. coli expressing the completed pathway, and assess the ability of feedback control to improve pathway yields. To confirm that ELP-based controllers are indeed responsible, as a control TetR containing constructs are decoupled from regulation by addition of anhydrotetracyline (aTc). Since aTc allosterically prevents TetR binding to DNA, thereby removing its ability to control gene expression. At the conclusion of these studies, we expect to have designed and incorporated a synthetic, tunable negative feedback control in the mevalonate pathway, and evaluated its ability to improve production of taxadiene precursors.

This experiment optimizes the production process of valuable precursors for a number of compounds including taxadiene, a precursor of the potent anticancer drug Taxol. We anticipate that this work establish a design principle for a novel class of gene circuit leading to an expanded and more flexible toolkit for the control of metabolic pathways.

Potential Problems and Alternative Approaches.

Although the designed ELP controllers are anticipated to regulate gene expression of the pathways, their dynamic range may not be optimal for the production. For example, while a controller may have a 5-fold change in expression between OFF and ON, optimal production may require a higher baseline expression level for the OFF state. In those cases, we may need to supplement the gene circuit with additional constitutive promoters to ensure proper function. Analogous strategies of tuning plasmid copy number, and promoter expression strengths, among other strategies, may be applied to ensure that controllers display an appropriate range of expression. Another issue that may arise is poor dynamics that may be tackled by tuning the half-life of proteins involved in the circuit with degradation tags and similar approaches. To guide these circuit-level interventions, a simplified model of the system as previously described is used.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A method for controlling a targeted gene expression with an environmental trigger comprising the step of
 a. fusing a gene for elastin-like polypeptides (ELPs) to a gene for a transcription factor;
 b. cloning the fused gene of said ELPs and transcription factor into an expression system wherein said targeted gene expression is to be regulated;
 c. expressing the ELPs-transcription factor fused gene to produce an ELPs-transcription factor fusion protein; and
 d. initiating an environmental trigger causing the aggregation of ELPs-transcription factor fusion protein whereby said targeted gene expression is regulated.

2. The method according to claim 1, wherein the ELPs is fused to the N-terminus of the transcription factor.

3. The method according to claim 1, wherein the ELPs is fused to the C-terminus of the transcription factor.

4. The method according to claim 1, wherein the environmental trigger is a change of temperature, pH value, ionic strength, or a combination thereof.

5. The method according to claim 1, wherein said expression system is a bacteria.

6. The method according to claim 5, wherein said bacteria is *E. coli*.

7. The method according to claim 1, wherein said expression system is a yeast.

8. The method according to claim 1, wherein said expression system expresses a natural product or an analogue thereof.

9. The method according to claim 8, wherein said natural product is taxadiene or an analogue thereof.

10. A method for enhancing productivity of a natural product or an analogue thereof comprising the step of:
   a. fusing a gene for elastin-like polypeptides (ELPs) to a gene for a transcription factor;
   b. cloning the fused gene into an expression system wherein expression of gene for said natural product or an analogue thereof is to be regulated;
   c. expressing the ELPs-transcription factor fused gene to produce ELPs-transcription factor fusion protein; and
   d. initiating an environmental trigger causing the aggregation of ELPs-transcription factor fusion protein whereby expression of gene for said natural product or an analogue thereof is regulated.

11. The method according to claim 10, wherein the ELPs is fused to the N-terminus of the transcription factor.

12. The method according to claim 10, wherein the ELPs is fused to the C-terminus of the transcription factor.

13. The method according to claim 10, wherein the environmental trigger is a change of temperature, pH value, ionic strength, or a combination thereof.

14. The method according to claim 10, wherein said expression system is a bacteria.

15. The method according to claim 10, wherein said expression system is a yeast.

16. The method according to claim 10, wherein said natural product is taxadiene or an analogue thereof.

17. The method according to claim 1, wherein ELPs comprise a repeating sequence of (VPGXG)n wherein n is an integral number; X is any amino acid residue except proline, and X may be varied from subunit to subunit.

18. The method according to claim 10, wherein ELPs comprise a repeating sequence of (VPGXG)n wherein n is an integral number; X is any amino acid residue except proline, and X may be varied from subunit to subunit.

* * * * *

SEQUENCE LISTING

```
<160> NUMBER OF SEQ ID NOS: 19

<210> SEQ ID NO 1
<211> LENGTH: 54
<212> TYPE: DNA
<213> ORGANISM: Artificial Sequence
<220> FEATURE:
<223> OTHER INFORMATION: Linker sequence

<400> SEQUENCE: 1
ctagaaataa ttttaaggag gagtacatat gggctactga taatgatctt cagc            54

<210> SEQ ID NO 2
<211> LENGTH: 54
<212> TYPE: DNA
<213> ORGANISM: Artificial sequence
<220> FEATURE:
<223> OTHER INFORMATION: Linker sequence

<400> SEQUENCE: 2
tttattaaaa ttcctcctca tgtatacccg atgactatta ctagaagtcg agct            54

<210> SEQ ID NO 3
<211> LENGTH: 75
<212> TYPE: DNA
<213> ORGANISM: Artificial sequence
<220> FEATURE:
<223> OTHER INFORMATION: Acidic ELP sequence

<400> SEQUENCE: 3
cgtgggcgtt ccgggtatcg gtgttccggg tatcggtgtt ccgggtgaag gtgttccggg    60
tatcggtgtg ccggg                                                      75
```

<210> SEQ ID NO 4
<211> LENGTH: 74
<212> TYPE: DNA
<213> ORGANISM: Artificial sequence
<220> FEATURE:
<223> OTHER INFORMATION: Basic ELP sequence

<400> SEQUENCE: 4
cgtgggtgtt ccgggccacg gtgtcccagg tggcggcgta ccgggccacg gtgttcctgg    60
tgctgcgtgc cggg                                                      74

<210> SEQ ID NO 5
<211> LENGTH: 75
<212> TYPE: DNA
<213> ORGANISM: Artificial sequence
<220> FEATURE:
<223> OTHER INFORMATION: Neutral ELP sequence

<400> SEQUENCE: 5
cgtgggtgtt ccgggcgttg gtgtcccagg tgttggcgta ccgggcgttg gtgttcctgg    60
tgttggcgtg ccggg                                                     75

<210> SEQ ID NO 6
<211> LENGTH: 551
<212> TYPE: PRT
<213> ORGANISM: Artificial sequence
<220> FEATURE:
<223> OTHER INFORMATION: GST-ELP

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Ala Met Val Pro

```
                210                 215                 220
Ala Met Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
    290                 295                 300

Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
            340                 345                 350

Pro Gly Val Gly Val Pro Gly Val Gly Val Pro Gly Val Gly Val Pro
        355                 360                 365

Gly Val Gly Val Pro Gly Val Gly Val Pro Gly Val Gly Val Pro Gly
    370                 375                 380

Val Gly Val Pro Gly Val Gly Val Pro Gly Val Gly Val Pro Gly Val
385                 390                 395                 400

Gly Val Pro Gly Val Gly Val Pro Gly Val Gly Val Pro Gly Val Gly
                405                 410                 415

Val Pro Gly Val Gly Val Pro Gly Val Gly Val Pro Gly Val Gly Val
            420                 425                 430

Pro Gly Val Gly Val Pro Gly Val Gly Val Pro Gly Val Gly Val Pro
        435                 440                 445

Gly Val Gly Val Pro Gly Val Gly Val Pro Gly Val Gly Val Pro Gly
    450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
                485                 490                 495

Val Pro Gly Val Gly Val Pro Gly Val Gly Val Pro Gly Val Gly Val
            500                 505                 510

Pro Gly Val Gly Val Pro Gly Val Gly Val Pro Gly Val Gly Val Pro
        515                 520                 525

Gly Val Gly Val Pro Gly Val Gly Val Pro Gly Val Gly Val Pro Gly
    530                 535                 540

Val Gly Val Pro Gly Val Gly
545                 550

<210> SEQ ID NO 7
<211> LENGTH: 388
<212> TYPE: PRT
<213> ORGANISM: Artificial sequence
<220> FEATURE:
<223> OTHER INFORMATION: RGD-ELP

<400> SEQUENCE: 7

Met Ala Ser Met Thr Gly Gly Gln Gln Met Gly His His His His
1               5                   10                  15

His His Asp Asp Asp Asp Lys Leu Asp Tyr Ala Val Thr Gly Arg Gly
```

```
            20                  25                  30
Asp Ser Pro Ala Ser Ser Lys Pro Ile Ala Val Pro Gly Ile Gly Val
         35                  40                  45

Pro Gly Ile Gly Val Pro Gly Lys Gly Val Pro Gly Ile Gly Val Pro
 50                  55                  60

Gly Ile Gly Val Pro Gly Ile Gly Val Pro Gly Ile Gly Val Pro Gly
 65                  70                  75                  80

Lys Gly Val Pro Gly Ile Gly Val Pro Gly Ile Gly Val Pro Gly Ile
                 85                  90                  95

Gly Val Pro Gly Ile Gly Val Pro Gly Lys Gly Val Pro Gly Ile Gly
            100                 105                 110

Val Pro Gly Ile Gly Val Pro Gly Ile Gly Val Pro Gly Ile Gly Val
            115                 120                 125

Pro Gly Lys Gly Val Pro Gly Ile Gly Val Pro Gly Ile Gly Val Pro
            130                 135                 140

Leu Asp Tyr Ala Val Thr Gly Arg Gly Asp Ser Pro Ala Ser Ser Lys
145                 150                 155                 160

Pro Ile Ala Val Pro Gly Ile Gly Val Pro Gly Ile Gly Val Pro Gly
                165                 170                 175

Lys Gly Val Pro Gly Ile Gly Val Pro Gly Ile Gly Val Pro Gly Ile
            180                 185                 190

Gly Val Pro Gly Ile Gly Val Pro Gly Lys Gly Val Pro Gly Ile Gly
            195                 200                 205

Val Pro Gly Ile Gly Val Pro Gly Ile Gly Val Pro Gly Ile Gly Val
            210                 215                 220

Pro Gly Lys Gly Val Pro Gly Ile Gly Val Pro Gly Ile Gly Val Pro
225                 230                 235                 240

Gly Ile Gly Val Pro Gly Ile Gly Val Pro Gly Lys Gly Val Pro Gly
                245                 250                 255

Ile Gly Val Pro Gly Ile Gly Val Pro Leu Asp Tyr Ala Val Thr Gly
            260                 265                 270

Arg Gly Asp Ser Pro Ala Ser Ser Lys Pro Ile Ala Val Pro Gly Ile
            275                 280                 285

Gly Val Pro Gly Ile Gly Val Pro Gly Lys Gly Val Pro Gly Ile Gly
            290                 295                 300

Val Pro Gly Ile Gly Val Pro Gly Ile Gly Val Pro Gly Ile Gly Val
305                 310                 315                 320

Pro Gly Lys Gly Val Pro Gly Ile Gly Val Pro Gly Ile Gly Val Pro
                325                 330                 335

Gly Ile Gly Val Pro Gly Ile Gly Val Pro Gly Lys Gly Val Pro Gly
            340                 345                 350

Ile Gly Val Pro Gly Ile Gly Val Pro Gly Ile Gly Val Pro Gly Ile
            355                 360                 365

Gly Val Pro Gly Lys Gly Val Pro Gly Ile Gly Val Pro Gly Ile Gly
            370                 375                 380

Val Pro Leu Glu
385

<210> SEQ ID NO 8
<211> LENGTH: 555
<212> TYPE: PRT
<213> ORGANISM: Artificial sequence
<220> FEATURE:
<223> OTHER INFORMATION: Sigma factor-ELP180
```

<400> SEQUENCE: 8

```
Met Asp Ala Met Val Pro Ala Met Val Pro Gly Val Gly Val Pro Gly
1               5                   10                  15
Val Gly Val Pro Gly Val Gly Val Pro Gly Val Gly Val Pro Gly Val
            20                  25                  30
Gly Val Pro Gly Val Gly Val Pro Gly Val Gly Val Pro Gly Val Gly
        35                  40                  45
Val Pro Gly Val Gly Val Pro Gly Val Gly Val Pro Gly Val Gly Val
    50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
            85                  90                  95
Val Gly Val Pro Gly Val Gly Val Pro Gly Val Gly Val Pro Gly Val
            100                 105                 110
Gly Val Pro Gly Val Gly Val Pro Gly Val Gly Val Pro Gly Val Gly
        115                 120                 125
Val Pro Gly Val Gly Val Pro Gly Val Gly Val Pro Gly Val Gly Val
    130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
            165                 170                 175
Val Gly Val Pro Gly Val Gly Val Pro Gly Val Gly Val Pro Gly Val
            180                 185                 190
Gly Val Pro Gly Val Gly Val Pro Gly Val Gly Val Pro Gly Val Gly
        195                 200                 205
Val Pro Gly Val Gly Val Pro Gly Val Gly Val Pro Gly Val Gly Val
    210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
            245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Lys Gly Glu
            325                 330                 335
Phe Gly Gly Gly Met Gly Ser Ser His His His His His His Ser Ser
            340                 345                 350
Gly Leu Glu Val Leu Phe Gln Gly Pro His Met Asn Glu Thr Asp Pro
        355                 360                 365
Asp Leu Glu Leu Leu Lys Arg Ile Gly Asn Asn Asp Ala Gln Ala Val
    370                 375                 380
Lys Glu Met Val Thr Arg Lys Leu Pro Arg Leu Leu Ala Leu Ala Ser
385                 390                 395                 400
Arg Leu Leu Gly Asp Ala Asp Glu Ala Arg Asp Ile Ala Gln Glu Ser
            405                 410                 415
```

```
Phe Leu Arg Ile Trp Lys Gln Ala Ala Ser Trp Arg Ser Glu Gln Ala
                420                 425                 430

Arg Phe Asp Thr Trp Leu His Arg Val Ala Leu Asn Leu Cys Tyr Asp
            435                 440                 445

Arg Leu Arg Arg Arg Lys Glu His Val Pro Val Asp Ser Glu His Ala
        450                 455                 460

Cys Glu Ala Leu Asp Thr Arg Pro Ala Pro Asp Glu Gln Leu Glu Ala
465                 470                 475                 480

Ser Ala Gln Ser Arg Arg Met Ala Gln Ala Leu Asp Gln Leu Pro Asp
                485                 490                 495

Arg Gln Arg Glu Ala Ile Val Leu Gln Tyr Tyr Gln Glu Leu Ser Asn
            500                 505                 510

Thr Glu Ala Ala Ala Leu Met Gln Ile Ser Val Glu Ala Leu Glu Ser
        515                 520                 525

Leu Leu Ser Arg Ala Arg Arg Asn Leu Arg Ser His Leu Ala Glu Ala
    530                 535                 540

Pro Gly Ala Asp Leu Ser Gly Arg Arg Lys Pro
545                 550                 555

<210> SEQ ID NO 9
<211> LENGTH: 800
<212> TYPE: PRT
<213> ORGANISM: Artificial sequence
<220> FEATURE:
<223> OTHER INFORMATION: an acidic ELP

<400> SEQUENCE: 9

Gly Val Gly Val Pro Gly Ile Gly Val Pro Gly Ile Gly Val Pro Gly
1               5                   10                  15

Glu Gly Val Pro Gly Ile Gly Val Pro Gly Val Gly Val Pro Gly Ile
            20                  25                  30

Gly Val Pro Gly Ile Gly Val Pro Gly Glu Gly Val Pro Gly Ile Gly
        35                  40                  45

Val Pro Gly Val Gly Val Pro Gly Ile Gly Val Pro Gly Ile Gly Val
    50                  55                  60

Pro Gly Glu Gly Val Pro Gly Ile Gly Val Pro Gly Val Gly Val Pro
65                  70                  75                  80

Gly Ile Gly Val Pro Gly Ile Gly Val Pro Gly Glu Gly Val Pro Gly
                85                  90                  95

Ile Gly Val Pro Gly Val Gly Val Pro Gly Ile Gly Val Pro Gly Ile
            100                 105                 110

Gly Val Pro Gly Glu Gly Val Pro Gly Ile Gly Val Pro Gly Val Gly
        115                 120                 125

Val Pro Gly Ile Gly Val Pro Gly Ile Gly Val Pro Gly Glu Gly Val
    130                 135                 140

Pro Gly Ile Gly Val Pro Gly Val Gly Val Pro Gly Ile Gly Val Pro
145                 150                 155                 160

Gly Ile Gly Val Pro Gly Glu Gly Val Pro Gly Ile Gly Val Pro Gly
                165                 170                 175

Val Gly Val Pro Gly Ile Gly Val Pro Gly Ile Gly Val Pro Gly Glu
            180                 185                 190

Gly Val Pro Gly Ile Gly Val Pro Gly Val Gly Val Pro Gly Ile Gly
        195                 200                 205

Val Pro Gly Ile Gly Val Pro Gly Glu Gly Val Pro Gly Ile Gly Val
    210                 215                 220
```

```
Pro Gly Val Gly Val Pro Gly Ile Gly Val Pro Gly Ile Gly Val Pro
225                 230                 235                 240

Gly Glu Gly Val Pro Gly Ile Gly Val Pro Gly Val Gly Val Pro Gly
                245                 250                 255

Ile Gly Val Pro Gly Ile Gly Val Pro Gly Glu Gly Val Pro Gly Ile
            260                 265                 270

Gly Val Pro Gly Val Gly Val Pro Gly Ile Gly Val Pro Gly Ile Gly
        275                 280                 285

Val Pro Gly Glu Gly Val Pro Gly Ile Gly Val Pro Gly Val Gly Val
    290                 295                 300

Pro Gly Ile Gly Val Pro Gly Ile Gly Val Pro Gly Glu Gly Val Pro
305                 310                 315                 320

Gly Ile Gly Val Pro Gly Val Gly Val Pro Gly Ile Gly Val Pro Gly
                325                 330                 335

Ile Gly Val Pro Gly Glu Gly Val Pro Gly Ile Gly Val Pro Gly Val
            340                 345                 350

Gly Val Pro Gly Ile Gly Val Pro Gly Ile Gly Val Pro Gly Glu Gly
        355                 360                 365

Val Pro Gly Ile Gly Val Pro Gly Val Gly Val Pro Gly Ile Gly Val
    370                 375                 380

Pro Gly Ile Gly Val Pro Gly Glu Gly Val Pro Gly Ile Gly Val Pro
385                 390                 395                 400

Gly Val Gly Val Pro Gly Ile Gly Val Pro Gly Ile Gly Val Pro Gly
                405                 410                 415

Glu Gly Val Pro Gly Ile Gly Val Pro Gly Val Gly Val Pro Gly Ile
            420                 425                 430

Gly Val Pro Gly Ile Gly Val Pro Gly Glu Gly Val Pro Gly Ile Gly
        435                 440                 445

Val Pro Gly Val Gly Val Pro Gly Ile Gly Val Pro Gly Ile Gly Val
    450                 455                 460

Pro Gly Glu Gly Val Pro Gly Ile Gly Val Pro Gly Val Gly Val Pro
465                 470                 475                 480

Gly Ile Gly Val Pro Gly Ile Gly Val Pro Gly Glu Gly Val Pro Gly
                485                 490                 495

Ile Gly Val Pro Gly Val Gly Val Pro Gly Ile Gly Val Pro Gly Ile
            500                 505                 510

Gly Val Pro Gly Glu Gly Val Pro Gly Ile Gly Val Pro Gly Val Gly
        515                 520                 525

Val Pro Gly Ile Gly Val Pro Gly Ile Gly Val Pro Gly Glu Gly Val
    530                 535                 540

Pro Gly Ile Gly Val Pro Gly Val Gly Val Pro Gly Ile Gly Val Pro
545                 550                 555                 560

Gly Ile Gly Val Pro Gly Glu Gly Val Pro Gly Ile Gly Val Pro Gly
                565                 570                 575

Val Gly Val Pro Gly Ile Gly Val Pro Gly Ile Gly Val Pro Gly Glu
            580                 585                 590

Gly Val Pro Gly Ile Gly Val Pro Gly Val Gly Val Pro Gly Ile Gly
        595                 600                 605

Val Pro Gly Ile Gly Val Pro Gly Glu Gly Val Pro Gly Ile Gly Val
    610                 615                 620

Pro Gly Val Gly Val Pro Gly Ile Gly Val Pro Gly Ile Gly Val Pro
625                 630                 635                 640
```

```
Gly Glu Gly Val Pro Gly Ile Gly Val Pro Gly Val Gly Val Pro Gly
                645                 650                 655

Ile Gly Val Pro Gly Ile Gly Val Pro Gly Glu Gly Val Pro Gly Ile
            660                 665                 670

Gly Val Pro Gly Val Gly Val Pro Gly Ile Gly Val Pro Gly Ile Gly
        675                 680                 685

Val Pro Gly Glu Gly Val Pro Gly Ile Gly Val Pro Gly Val Gly Val
    690                 695                 700

Pro Gly Ile Gly Val Pro Gly Ile Gly Val Pro Gly Glu Gly Val Pro
705                 710                 715                 720

Gly Ile Gly Val Pro Gly Val Gly Val Pro Gly Ile Gly Val Pro Gly
            725                 730                 735

Ile Gly Val Pro Gly Glu Gly Val Pro Gly Ile Gly Val Pro Gly Val
        740                 745                 750

Gly Val Pro Gly Ile Gly Val Pro Gly Ile Gly Val Pro Gly Glu Gly
    755                 760                 765

Val Pro Gly Ile Gly Val Pro Gly Val Gly Val Pro Gly Ile Gly Val
770                 775                 780

Pro Gly Ile Gly Val Pro Gly Glu Gly Val Pro Gly Ile Gly Val Pro
785                 790                 795                 800

<210> SEQ ID NO 10
<211> LENGTH: 400
<212> TYPE: PRT
<213> ORGANISM: Artificial sequence
<220> FEATURE:
<223> OTHER INFORMATION: a basic ELP

<400> SEQUENCE: 10

Gly Val Gly Val Pro Gly His Gly Val Pro Gly Gly Gly Val Pro Gly
1               5                   10                  15

His Gly Val Pro Gly Ala Gly Val Pro Gly Val Gly Val Pro Gly His
            20                  25                  30

Gly Val Pro Gly Gly Gly Val Pro Gly His Gly Val Pro Gly Ala Gly
        35                  40                  45

Val Pro Gly Val Gly Val Pro Gly His Gly Val Pro Gly Gly Gly Val
    50                  55                  60

Pro Gly His Gly Val Pro Gly Ala Gly Val Pro Gly Val Gly Val Pro
65                  70                  75                  80

Gly His Gly Val Pro Gly Gly Gly Val Pro Gly His Gly Val Pro Gly
            85                  90                  95

Ala Gly Val Pro Gly Val Gly Val Pro Gly His Gly Val Pro Gly Gly
        100                 105                 110

Gly Val Pro Gly His Gly Val Pro Gly Ala Gly Val Pro Gly Val Gly
    115                 120                 125

Val Pro Gly His Gly Val Pro Gly Gly Gly Val Pro Gly His Gly Val
    130                 135                 140

Pro Gly Ala Gly Val Pro Gly Val Gly Val Pro Gly His Gly Val Pro
145                 150                 155                 160

Gly Gly Gly Val Pro Gly His Gly Val Pro Gly Ala Gly Val Pro Gly
            165                 170                 175

Val Gly Val Pro Gly His Gly Val Pro Gly Gly Gly Val Pro Gly His
        180                 185                 190

Gly Val Pro Gly Ala Gly Val Pro Gly Val Gly Val Pro Gly His Gly
    195                 200                 205
```

Val Pro Gly Gly Val Pro Gly His Gly Val Pro Gly Ala Gly Val
        210                 215                 220

Pro Gly Val Gly Val Pro Gly His Gly Val Pro Gly Gly Val Pro
225                 230                 235                 240

Gly His Gly Val Pro Gly Ala Gly Val Pro Gly Val Gly Val Pro Gly
                245                 250                 255

His Gly Val Pro Gly Gly Val Pro Gly His Gly Val Pro Gly Ala
                260                 265                 270

Gly Val Pro Gly Val Gly Val Pro Gly His Gly Val Pro Gly Gly
                275                 280                 285

Val Pro Gly His Gly Val Pro Gly Ala Gly Val Pro Gly Val Gly Val
        290                 295                 300

Pro Gly His Gly Val Pro Gly Gly Val Pro Gly His Gly Val Pro
305                 310                 315                 320

Gly Ala Gly Val Pro Gly Val Gly Val Pro Gly His Gly Val Pro Gly
                325                 330                 335

Gly Gly Val Pro Gly His Gly Val Pro Gly Ala Gly Val Pro Gly Val
                340                 345                 350

Gly Val Pro Gly His Gly Val Pro Gly Gly Val Pro Gly His Gly
                355                 360                 365

Val Pro Gly Ala Gly Val Pro Gly Val Gly Val Pro Gly His Gly Val
        370                 375                 380

Pro Gly Gly Val Pro Gly His Gly Val Pro Gly Ala Gly Val Pro
385                 390                 395                 400

<210> SEQ ID NO 11
<211> LENGTH: 800
<212> TYPE: PRT
<213> ORGANISM: Artificial sequence
<220> FEATURE:
<223> OTHER INFORMATION: a neutral ELP

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
        20                  25                  30

Gly Val Pro Gly Val Gly Val Pro Gly Val Gly Val Pro Gly Val Gly
                35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
                115                 120                 125

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

-continued

Val Gly Val Pro Gly Val Gly Val Pro Gly Val Gly Val
            180             185             190

Gly Val Pro Gly Val Gly Val Pro Gly Val Gly Val Pro Gly Val Gly
        195             200             205

Val Pro Gly Val Gly Val Pro Gly Val Gly Val Pro Gly Val Gly Val
    210             215             220

Pro Gly Val Gly Val Pro Gly Val Gly Val Pro Gly Val Gly Val Pro
225             230             235             240

Gly Val Gly Val Pro Gly Val Gly Val Pro Gly Val Gly Val Pro Gly
        245             250             255

Val Gly Val Pro Gly Val Gly Val Pro Gly Val Gly Val Pro Gly Val
    260             265             270

Gly Val Pro Gly Val Gly Val Pro Gly Val Gly Val Pro Gly Val Gly
        275             280             285

Val Pro Gly Val Gly Val Pro Gly Val Gly Val Pro Gly Val Gly Val
    290             295             300

Pro Gly Val Gly Val Pro Gly Val Gly Val Pro Gly Val Gly Val Pro
305             310             315             320

Gly Val Gly Val Pro Gly Val Gly Val Pro Gly Val Gly Val Pro Gly
        325             330             335

Val Gly Val Pro Gly Val Gly Val Pro Gly Val Gly Val Pro Gly Val
    340             345             350

Gly Val Pro Gly Val Gly Val Pro Gly Val Gly Val Pro Gly Val Gly
        355             360             365

Val Pro Gly Val Gly Val Pro Gly Val Gly Val Pro Gly Val Gly Val
    370             375             380

Pro Gly Val Gly Val Pro Gly Val Gly Val Pro Gly Val Gly Val Pro
385             390             395             400

Gly Val Gly Val Pro Gly Val Gly Val Pro Gly Val Gly Val Pro Gly
        405             410             415

Val Gly Val Pro Gly Val Gly Val Pro Gly Val Gly Val Pro Gly Val
    420             425             430

Gly Val Pro Gly Val Gly Val Pro Gly Val Gly Val Pro Gly Val Gly
        435             440             445

Val Pro Gly Val Gly Val Pro Gly Val Gly Val Pro Gly Val Gly Val
    450             455             460

Pro Gly Val Gly Val Pro Gly Val Gly Val Pro Gly Val Gly Val Pro
465             470             475             480

Gly Val Gly Val Pro Gly Val Gly Val Pro Gly Val Gly Val Pro Gly
        485             490             495

Val Gly Val Pro Gly Val Gly Val Pro Gly Val Gly Val Pro Gly Val
    500             505             510

Gly Val Pro Gly Val Gly Val Pro Gly Val Gly Val Pro Gly Val Gly
        515             520             525

Val Pro Gly Val Gly Val Pro Gly Val Gly Val Pro Gly Val Gly Val
    530             535             540

Pro Gly Val Gly Val Pro Gly Val Gly Val Pro Gly Val Gly Val Pro
545             550             555             560

Gly Val Gly Val Pro Gly Val Gly Val Pro Gly Val Gly Val Pro Gly
        565             570             575

Val Gly Val Pro Gly Val Gly Val Pro Gly Val Gly Val Pro Gly Val
    580             585             590

Gly Val Pro Gly Val Gly Val Pro Gly Val Gly Val Pro Gly Val Gly

```
                595                 600                 605
Val Pro Gly Val Gly Val Pro Gly Val Gly Val Pro Gly Val Gly Val
            610                 615                 620

Pro Gly Val Gly Val Pro Gly Val Gly Val Pro Gly Val Gly Val Pro
625                 630                 635                 640

Gly Val Gly Val Pro Gly Val Gly Val Pro Gly Val Gly Val Pro Gly
                645                 650                 655

Val Gly Val Pro Gly Val Gly Val Pro Gly Val Gly Val Pro Gly Val
            660                 665                 670

Gly Val Pro Gly Val Gly Val Pro Gly Val Gly Val Pro Gly Val Gly
        675                 680                 685

Val Pro Gly Val Gly Val Pro Gly Val Gly Val Pro Gly Val Gly Val
    690                 695                 700

Pro Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
                725                 730                 735

Val Gly Val Pro Gly Val Gly Val Pro Gly Val Gly Val Pro Gly Val
            740                 745                 750

Gly Val Pro Gly Val Gly Val Pro Gly Val Gly Val Pro Gly Val Gly
        755                 760                 765

Val Pro Gly Val Gly Val Pro Gly Val Gly Val Pro Gly Val Gly Val
    770                 775                 780

Pro Gly Val Gly Val Pro Gly Val Gly Val Pro Gly Val Gly Val Pro
785                 790                 795                 800

<210> SEQ ID NO 12
<211> LENGTH: 215
<212> TYPE: PRT
<213> ORGANISM: Artificial sequence
<220> FEATURE:
<223> OTHER INFORMATION: Sigma factor

<400> SEQUENCE: 12

Met Gly Ser Ser His His His His His His Ser Gly Leu Glu Val
1               5                   10                  15

Leu Phe Gln Gly Pro His Met Asn Glu Thr Asp Pro Asp Leu Glu Leu
            20                  25                  30

Leu Lys Arg Ile Gly Asn Asn Asp Ala Gln Ala Val Lys Glu Met Val
        35                  40                  45

Thr Arg Lys Leu Pro Arg Leu Leu Ala Leu Ala Ser Arg Leu Leu Gly
    50                  55                  60

Asp Ala Asp Glu Ala Arg Asp Ile Ala Gln Glu Ser Phe Leu Arg Ile
65                  70                  75                  80

Trp Lys Gln Ala Ala Ser Trp Arg Ser Glu Gln Ala Arg Phe Asp Thr
                85                  90                  95

Trp Leu His Arg Val Ala Leu Asn Leu Cys Tyr Asp Arg Leu Arg Arg
            100                 105                 110

Arg Lys Glu His Val Pro Val Asp Ser Glu His Ala Cys Glu Ala Leu
        115                 120                 125

Asp Thr Arg Pro Ala Pro Asp Glu Gln Leu Glu Ala Ser Ala Gln Ser
    130                 135                 140

Arg Arg Met Ala Gln Ala Leu Asp Gln Leu Pro Asp Arg Gln Arg Glu
145                 150                 155                 160

Ala Ile Val Leu Gln Tyr Tyr Gln Glu Leu Ser Asn Thr Glu Ala Ala
```

```
                165                 170                 175
Ala Leu Met Gln Ile Ser Val Glu Ala Leu Glu Ser Leu Leu Ser Arg
            180                 185                 190

Ala Arg Arg Asn Leu Arg Ser His Leu Ala Glu Ala Pro Gly Ala Asp
        195                 200                 205

Leu Ser Gly Arg Arg Lys Pro
    210                 215

<210> SEQ ID NO 13
<211> LENGTH: 1653
<212> TYPE: DNA
<213> ORGANISM: Artificial sequence
<220> FEATURE:
<223> OTHER INFORMATION: GST-ELP

<400> SEQUENCE: 13
```

| | | | | | |
|---|---|---|---|---|---|
| atgtcccta | tactaggtta | ttggaaaatt | aagggccttg | tgcaacccac | tcgacttctt | 60 |
| ttggaatatc | ttgaagaaaa | atatgaagag | catttgtatg | agcgcgatga | aggtgataaa | 120 |
| tggcgaaaca | aaaagtttga | attgggtttg | gagtttccca | atcttcctta | ttatattgat | 180 |
| ggtgatgtta | aattaacaca | gtctatggcc | atcatacgtt | atatagctga | caagcacaac | 240 |
| atgttgggtg | gttgtccaaa | agagcgtgca | gagatttcaa | tgcttgaagg | agcggttttg | 300 |
| gatattagat | acggtgtttc | gagaattgca | tatagtaaag | actttgaaac | tctcaaagtt | 360 |
| gattttctta | gcaagctacc | tgaaatgctg | aaaatgttcg | aagatcgttt | atgtcataaa | 420 |
| acatatttaa | atggtgatca | tgtaacccat | cctgacttca | tgttgtatga | cgctcttgat | 480 |
| gttgttttat | acatggaccc | aatgtgcctg | gatgcgttcc | caaaattagt | ttgtttttaaa | 540 |
| aaacgtattg | aagctatccc | acaaattgat | aagtacttga | atccagcaa | gtatatagca | 600 |
| tggcctttgc | agggctggca | agccacgttt | ggtggtggcg | accatcctcc | aaaatcggat | 660 |
| gccatggtac | ctgctatggt | cccgggtgtt | ggtgtgccag | gcgttggtgt | gccgggtgtt | 720 |
| ggtgtgccag | gcgttggtgt | cccgggtgtt | ggtgtgccag | gcgttggtgt | gccgggtgtt | 780 |
| ggtgtgccag | gcgttggtgt | cccgggtgtt | ggtgtgccag | gcgttggtgt | gccgggtgtt | 840 |
| ggtgtgccag | gcgttggtgt | cccgggtgtt | ggtgtgccag | gcgttggtgt | gccgggtgtt | 900 |
| ggtgtgccag | gcgttggtgt | cccgggtgtt | ggtgtgccag | gcgttggtgt | gccgggtgtt | 960 |
| ggtgtgccag | gcgttggtgt | cccgggtgtt | ggtgtgccag | gcgttggtgt | gccgggtgtt | 1020 |
| ggtgtgccag | gcgttggtgt | cccgggtgtt | ggtgtgccag | gcgttggtgt | gccgggtgtt | 1080 |
| ggtgtgccag | gcgttggtgt | cccgggtgtt | ggtgtgccag | gcgttggtgt | gccgggtgtt | 1140 |
| ggtgtgccag | gcgttggtgt | cccgggtgtt | ggtgtgccag | gcgttggtgt | gccgggtgtt | 1200 |
| ggtgtgccag | gcgttggtgt | cccgggtgtt | ggtgtgccag | gcgttggtgt | gccgggtgtt | 1260 |
| ggtgtgccag | gcgttggtgt | cccgggtgtt | ggtgtgccag | gcgttggtgt | gccgggtgtt | 1320 |
| ggtgtgccag | gcgttggtgt | cccgggtgtt | ggtgtgccag | gcgttggtgt | gccgggtgtt | 1380 |
| ggtgtgccag | gcgttggtgt | cccgggtgtt | ggtgtgccag | gcgttggtgt | gccgggtgtt | 1440 |
| ggtgtgccag | gcgttggtgt | cccgggtgtt | ggtgtgccag | gcgttggtgt | gccgggtgtt | 1500 |
| ggtgtgccag | gcgttggtgt | cccgggtgtt | ggtgtgccag | gcgttggtgt | gccgggtgtt | 1560 |
| ggtgtgccag | gcgttggtgt | cccgggtgtt | ggtgtgccag | gcgttggtgt | gccgggtgtt | 1620 |
| ggtgtgccag | gcgttggtgt | cccgggtgtt | ggt | | | 1653 |

```
<210> SEQ ID NO 14
```

<211> LENGTH: 1167
<212> TYPE: DNA
<213> ORGANISM: Artificial sequence
<220> FEATURE:
<223> OTHER INFORMATION: RGD-ELP

<400> SEQUENCE: 14

| | |
|---|---|
| atggctagca tgactggtgg acagcaaatg ggtcaccacc accaccacca ccatgatgat | 60 |
| gatgataaac tcgactatgc tgtcactggc cgtggagaca gccccgcaag cagcaagcca | 120 |
| attgcggtgc cgggtatcgg cgttccgggc atcggtgtac cgggcaaagg tgttccgggc | 180 |
| atcggtgttc cgggtatcgg ggtgccgggt atcggcgttc cgggcatcgg tgtaccgggc | 240 |
| aaaggtgttc cgggcatcgg tgttccgggt atcggggtgc cgggtatcgg cgttccgggc | 300 |
| atcggtgtac cgggcaaagg tgttccgggc atcggtgttc cgggtatcgg ggtgccgggt | 360 |
| atcggcgttc cgggcatcgg tgtaccgggc aaaggtgttc cgggcatcgg tgttccgggt | 420 |
| atcggggtgc cgctcgacta tgctgtcact ggccgtggag acagccccgc aagcagcaag | 480 |
| ccaattgcgg tgccgggtat cggcgttccg ggcatcggt taccgggcaa aggtgttccg | 540 |
| ggcatcggtg ttccgggtat cggggtgccg ggtatcggcg ttccgggcat cggtgtaccg | 600 |
| ggcaaaggtg ttccgggcat cggtgttccg ggtatcgggg tgccgggtat cggcgttccg | 660 |
| ggcatcggtg taccgggcaa aggtgttccg ggcatcggtg ttccgggtat cggggtgccg | 720 |
| ggtatcggcg ttccgggcat cggtgtaccg ggcaaaggtg ttccgggcat cggtgttccg | 780 |
| ggtatcgggg tgccgctcga ctatgctgtc actggccgtg agacagccc cgcaagcagc | 840 |
| aagccaattg cggtgccggg tatcggcgtt ccgggcatcg tgtaccggg caaaggtgtt | 900 |
| ccgggcatcg gtgttccggg tatcggggtg ccgggtatcg cgttccggg catcggtgta | 960 |
| ccgggcaaag gtgttccggg catcggtgtt ccgggtatcg gggtgccggg tatcggcgtt | 1020 |
| ccgggcatcg gtgtaccggg caaaggtgtt ccgggcatcg gtgttccggg tatcggggtg | 1080 |
| ccgggtatcg gcgttccggg catcggtgta ccgggcaaag gtgttccggg catcggtgtt | 1140 |
| ccgggtatcg gggtgccgct cgagtaa | 1167 |

<210> SEQ ID NO 15
<211> LENGTH: 1668
<212> TYPE: DNA
<213> ORGANISM: Artificial sequence
<220> FEATURE:
<223> OTHER INFORMATION: Sigma factor ELP180

<400> SEQUENCE: 15

| | |
|---|---|
| atggatgcca tggtacctgc tatggtcccg ggtgttggtg tgccaggcgt tggtgtgccg | 60 |
| ggtgttggtg tgccaggcgt tggtgtcccg ggtgttggtg tgccaggcgt tggtgtgccg | 120 |
| ggtgttggtg tgccaggcgt tggtgtcccg ggtgttggtg tgccaggcgt tggtgtgccg | 180 |
| ggtgttggtg tgccaggcgt tggtgtcccg ggtgttggtg tgccaggcgt tggtgtgccg | 240 |
| ggtgttggtg tgccaggcgt tggtgtcccg ggtgttggtg tgccaggcgt tggtgtgccg | 300 |
| ggtgttggtg tgccaggcgt tggtgtcccg ggtgttggtg tgccaggcgt tggtgtgccg | 360 |
| ggtgttggtg tgccaggcgt tggtgtcccg ggtgttggtg tgccaggcgt tggtgtgccg | 420 |
| ggtgttggtg tgccaggcgt tggtgtcccg ggtgttggtg tgccaggcgt tggtgtgccg | 480 |
| ggtgttggtg tgccaggcgt tggtgtcccg ggtgttggtg tgccaggcgt tggtgtgccg | 540 |
| ggtgttggtg tgccaggcgt tggtgtcccg ggtgttggtg tgccaggcgt tggtgtgccg | 600 |
| ggtgttggtg tgccaggcgt tggtgtcccg ggtgttggtg tgccaggcgt tggtgtgccg | 660 |

```
ggtgttggtg tgccaggcgt tggtgtcccg ggtgttggtg tgccaggcgt tggtgtgccg      720
ggtgttggtg tgccaggcgt tggtgtcccg ggtgttggtg tgccaggcgt tggtgtgccg      780
ggtgttggtg tgccaggcgt tggtgtcccg ggtgttggtg tgccaggcgt tggtgtgccg      840
ggtgttggtg tgccaggcgt tggtgtcccg ggtgttggtg tgccaggcgt tggtgtgccg      900
ggtgttggtg tgccaggcgt tggtgtcccg ggtgttggtg tgccaggcgt tggtgtgccg      960
ggtgttggtg tgccaggcgt tggtgtcccg ggtgttggta aaggagaatt cggcggtggc     1020
atgggcagca gccatcatca tcatcatcac agcagcggcc tggaagttct gttccagggg     1080
ccccatatga atgaaaccga tcctgatctg aactgctga aacgtattgg taataatgat      1140
gcacaggccg ttaaagaaat ggttacccgt aaactgcctc gtctgctggc actggcaagt     1200
cgcctgctgg gtgatgcaga tgaagcacgt gatattgcac aagaaagttt tctgcgcatt     1260
tggaaacagg cagcaagctg gcgtagcgaa caggcacgtt ttgataccctg ctgcatcgt    1320 gttgcactga atctgtgtta tgatcgtctg cgtcgtcgta aagaacatgt gccggttgat     1380
agcgaacatg cctgtgaagc actggatacc cgtccggcac cggatgaaca gctggaagca     1440
agcgcacaga gccgtcgtat ggcacaggca ctggatcagc tgccggatcg tcagcgtgaa     1500
gcaattgttc tgcagtatta tcaagaactg agcaataccg aagcagcagc actgatgcaa     1560
attagcgttg aagccctgga aagcctgctg agccgtgcac gtcgtaatct gcgtagccat     1620
ctggccgaag caccgggtgc agatctgagc ggtcgtcgca accgtaa                   1668

<210> SEQ ID NO 16
<211> LENGTH: 2400
<212> TYPE: DNA
<213> ORGANISM: Artificial sequence
<220> FEATURE:
<223> OTHER INFORMATION: Acidic ELP

<400> SEQUENCE: 16
ggcgtgggcg ttccgggtat cggtgttccg ggtatcggtg ttccgggtga aggtgttccg       60
ggtatcggtg tgccgggcgt gggcgttccg ggtatcggtg ttccgggtat cggtgttccg      120
ggtgaaggtg ttccgggtat cggtgtgccg ggcgtgggcg ttccgggtat cggtgttccg      180
ggtatcggtg ttccgggtga aggtgttccg ggtatcggtg tgccgggcgt gggcgttccg      240
ggtatcggtg ttccgggtat cggtgttccg ggtgaaggtg ttccgggtat cggtgtgccg      300
ggcgtgggcg ttccgggtat cggtgttccg ggtatcggtg ttccgggtga aggtgttccg      360
ggtatcggtg tgccgggcgt gggcgttccg ggtatcggtg ttccgggtat cggtgttccg      420
ggtgaaggtg ttccgggtat cggtgtgccg ggcgtgggcg ttccgggtat cggtgttccg      480
ggtatcggtg ttccgggtga aggtgttccg ggtatcggtg tgccgggcgt gggcgttccg      540
ggtatcggtg ttccgggtat cggtgttccg ggtgaaggtg ttccgggtat cggtgtgccg      600
ggcgtgggcg ttccgggtat cggtgttccg ggtatcggtg ttccgggtga aggtgttccg      660
ggtatcggtg tgccgggcgt gggcgttccg ggtatcggtg ttccgggtat cggtgttccg      720
ggtgaaggtg ttccgggtat cggtgtgccg ggcgtgggcg ttccgggtat cggtgttccg      780
ggtatcggtg ttccgggtga aggtgttccg ggtatcggtg tgccgggcgt gggcgttccg      840
ggtatcggtg ttccgggtat cggtgttccg ggtgaaggtg ttccgggtat cggtgtgccg      900
ggcgtgggcg ttccgggtat cggtgttccg ggtatcggtg ttccgggtga aggtgttccg      960
ggtatcggtg tgccgggcgt gggcgttccg ggtatcggtg ttccgggtat cggtgttccg     1020
```

```
ggtgaaggtg ttccgggtat cggtgtgccg ggcgtgggcg ttccgggtat cggtgttccg   1080
ggtatcggtg ttccgggtga aggtgttccg ggtatcggtg tgccgggcgt gggcgttccg   1140
ggtatcggtg ttccgggtat cggtgttccg ggtgaaggtg ttccgggtat cggtgtgccg   1200
ggcgtgggcg ttccgggtat cggtgttccg ggtatcggtg ttccgggtga aggtgttccg   1260
ggtatcggtg tgccgggcgt gggcgttccg ggtatcggtg ttccgggtat cggtgttccg   1320
ggtgaaggtg ttccgggtat cggtgtgccg ggcgtgggcg ttccgggtat cggtgttccg   1380
ggtatcggtg ttccgggtga aggtgttccg ggtatcggtg tgccgggcgt gggcgttccg   1440
ggtatcggtg ttccgggtat cggtgttccg ggtgaaggtg ttccgggtat cggtgtgccg   1500
ggcgtgggcg ttccgggtat cggtgttccg ggtatcggtg ttccgggtga aggtgttccg   1560
ggtatcggtg tgccgggcgt gggcgttccg ggtatcggtg ttccgggtat cggtgttccg   1620
ggtgaaggtg ttccgggtat cggtgtgccg ggcgtgggcg ttccgggtat cggtgttccg   1680
ggtatcggtg ttccgggtga aggtgttccg ggtatcggtg tgccgggcgt gggcgttccg   1740
ggtatcggtg ttccgggtat cggtgttccg ggtgaaggtg ttccgggtat cggtgtgccg   1800
ggcgtgggcg ttccgggtat cggtgttccg ggtatcggtg ttccgggtga aggtgttccg   1860
ggtatcggtg tgccgggcgt gggcgttccg ggtatcggtg ttccgggtat cggtgttccg   1920
ggtgaaggtg ttccgggtat cggtgtgccg ggcgtgggcg ttccgggtat cggtgttccg   1980
ggtatcggtg ttccgggtga aggtgttccg ggtatcggtg tgccgggcgt gggcgttccg   2040
ggtatcggtg ttccgggtat cggtgttccg ggtgaaggtg ttccgggtat cggtgtgccg   2100
ggcgtgggcg ttccgggtat cggtgttccg ggtatcggtg ttccgggtga aggtgttccg   2160
ggtatcggtg tgccgggcgt gggcgttccg ggtatcggtg ttccgggtat cggtgttccg   2220
ggtgaaggtg ttccgggtat cggtgtgccg ggcgtgggcg ttccgggtat cggtgttccg   2280
ggtatcggtg ttccgggtga aggtgttccg ggtatcggtg tgccgggcgt gggcgttccg   2340
ggtatcggtg ttccgggtat cggtgttccg ggtgaaggtg ttccgggtat cggtgtgccg   2400

<210> SEQ ID NO 17
<211> LENGTH: 1200
<212> TYPE: DNA
<213> ORGANISM: Artificial sequence
<220> FEATURE:
<223> OTHER INFORMATION: a basic ELP

<400> SEQUENCE: 17
ggcgtgggtg ttccgggcca cggtgtccca ggtggcggcg taccgggcca cggtgttcct     60
ggtgctggcg tgccgggcgt gggtgttccg ggccacggag tcccaggtgg cggcgtaccg    120
ggccacggtg ttcctggtgc tggcgtgccg ggcgtgggtg ttccgggcca cggtgtccca    180
ggtggcggcg taccgggcca cggtgttcct ggtgctggcg tgccgggcgt gggtgttccg    240
ggccacggag tcccaggtgg cggcgtaccg ggccacggtg ttcctggtgc tggcgtgccg    300
ggcgtgggtg ttccgggcca cggtgtccca ggtggcggcg taccgggcca cggtgttcct    360
ggtgctggcg tgccgggcgt gggtgttccg ggccacggag tcccaggtgg cggcgtaccg    420
ggccacggtg ttcctggtgc tggcgtgccg ggcgtgggtg ttccgggcca cggtgtccca    480
ggtggcggcg taccgggcca cggtgttcct ggtgctggcg tgccgggcgt gggtgttccg    540
ggccacggag tcccaggtgg cggcgtaccg ggccacggtg ttcctggtgc tggcgtgccg    600
ggcgtgggtg ttccgggcca cggtgtccca ggtggcggcg taccgggcca cggtgttcct    660
ggtgctggcg tgccgggcgt gggtgttccg ggccacggag tcccaggtgg cggcgtaccg    720
```

```
ggccacggtg ttcctggtgc tggcgtgccg ggcgtgggtg ttccgggcca cggtgtccca      780
ggtggcggcg taccgggcca cggtgttcct ggtgctggcg tgccgggcgt gggtgttccg      840
ggccacggag tcccaggtgg cggcgtaccg ggccacggtg ttcctggtgc tggcgtgccg      900
ggcgtgggtg ttccgggcca cggtgtccca ggtggcggcg taccgggcca cggtgttcct      960
ggtgctggcg tgccgggcgt gggtgttccg ggccacggag tcccaggtgg cggcgtaccg     1020
ggccacggtg ttcctggtgc tggcgtgccg ggcgtgggtg ttccgggcca cggtgtccca     1080
ggtggcggcg taccgggcca cggtgttcct ggtgctggcg tgccgggcgt gggtgttccg     1140
ggccacggag tcccaggtgg cggcgtaccg ggccacggtg ttcctggtgc tggcgtgccg     1200

<210> SEQ ID NO 18
<211> LENGTH: 2458
<212> TYPE: DNA
<213> ORGANISM: Artificial sequence
<220> FEATURE:
<223> OTHER INFORMATION: a neutral ELP

<400> SEQUENCE: 18
ctagaaataa ttttaaggag gagtacatat gggcgtgggt gttccgggcg ttggagtccc       60
aggtgttggc gtaccgggcg ttggtgttcc tggtgttggc gtgccgggcg tgggtgttcc      120
gggcgttgga gtcccaggtg ttggcgtacc gggcgttggt gttcctggtg ttggcgtgcc      180
gggcgtgggt gttccgggcg ttggagtccc aggtgttggc gtaccgggcg ttggtgttcc      240
tggtgttggc gtgccgggcg tgggtgttcc gggcgttgga gtcccaggtg ttggcgtacc      300
gggcgttggt gttcctggtg ttggcgtgcc gggcgtgggt gttccgggcg ttggagtccc      360
aggtgttggc gtaccgggcg ttggtgttcc tggtgttggc gtgccgggcg tgggtgttcc      420
gggcgttgga gtcccaggtg ttggcgtacc gggcgttggt gttcctggtg ttggcgtgcc      480
gggcgtgggt gttccgggcg ttggagtccc aggtgttggc gtaccgggcg ttggtgttcc      540
tggtgttggc gtgccgggcg tgggtgttcc gggcgttgga gtcccaggtg ttggcgtacc      600
gggcgttggt gttcctggtg ttggcgtgcc gggcgtgggt gttccgggcg ttggagtccc      660
aggtgttggc gtaccgggcg ttggtgttcc tggtgttggc gtgccgggcg tgggtgttcc      720
gggcgttgga gtcccaggtg ttggcgtacc gggcgttggt gttcctggtg ttggcgtgcc      780
gggcgtgggt gttccgggcg ttggagtccc aggtgttggc gtaccgggcg ttggtgttcc      840
tggtgttggc gtgccgggcg tgggtgttcc gggcgttgga gtcccaggtg ttggcgtacc      900
gggcgttggt gttcctggtg ttggcgtgcc gggcgtgggt gttccgggcg ttggagtccc      960
aggtgttggc gtaccgggcg ttggtgttcc tggtgttggc gtgccgggcg tgggtgttcc     1020
gggcgttgga gtcccaggtg ttggcgtacc gggcgttggt gttcctggtg ttggcgtgcc     1080
gggcgtgggt gttccgggcg ttggagtccc aggtgttggc gtaccgggcg ttggtgttcc     1140
tggtgttggc gtgccgggcg tgggtgttcc gggcgttgga gtcccaggtg ttggcgtacc     1200
gggcgttggt gttcctggtg ttggcgtgcc gggcgtgggt gttccgggcg ttggagtccc     1260
aggtgttggc gtaccgggcg ttggtgttcc tggtgttggc gtgccgggcg tgggtgttcc     1320
gggcgttgga gtcccaggtg ttggcgtacc gggcgttggt gttcctggtg ttggcgtgcc     1380
gggcgtgggt gttccgggcg ttggagtccc aggtgttggc gtaccgggcg ttggtgttcc     1440
tggtgttggc gtgccgggcg tgggtgttcc gggcgttgga gtcccaggtg ttggcgtacc     1500
gggcgttggt gttcctggtg ttggcgtgcc gggcgtgggt gttccgggcg ttggagtccc     1560
```

```
aggtgttggc gtaccgggcg ttggtgttcc tggtgttggc gtgccgggcg tgggtgttcc      1620
gggcgttgga gtcccaggtg ttggcgtacc gggcgttggt gttcctggtg ttggcgtgcc      1680
gggcgtgggt gttccgggcg ttggagtccc aggtgttggc gtaccgggcg ttggtgttcc      1740
tggtgttggc gtgccgggcg tgggtgttcc gggcgttgga gtcccaggtg ttggcgtacc      1800
gggcgttggt gttcctggtg ttggcgtgcc gggcgtgggt gttccgggcg ttggagtccc      1860
aggtgttggc gtaccgggcg ttggtgttcc tggtgttggc gtgccgggcg tgggtgttcc      1920
gggcgttgga gtcccaggtg ttggcgtacc gggcgttggt gttcctggtg ttggcgtgcc      1980
gggcgtgggt gttccgggcg ttggagtccc aggtgttggc gtaccgggcg ttggtgttcc      2040
tggtgttggc gtgccgggcg tgggtgttcc gggcgttgga gtcccaggtg ttggcgtacc      2100
gggcgttggt gttcctggtg ttggcgtgcc gggcgtgggt gttccgggcg ttggagtccc      2160
aggtgttggc gtaccgggcg ttggtgttcc tggtgttggc gtgccgggcg tgggtgttcc      2220
gggcgttgga gtcccaggtg ttggcgtacc gggcgttggt gttcctggtg ttggcgtgcc      2280
gggcgtgggt gttccgggcg ttggagtccc aggtgttggc gtaccgggcg ttggtgttcc      2340
tggtgttggc gtgccgggcg tgggtgttcc gggcgttgga gtcccaggtg ttggcgtacc      2400
gggcgttggt gttcctggtg ttggcgtgcc gggctactga taatgatctt cagctcga       2458

<210> SEQ ID NO 19
<211> LENGTH: 648
<212> TYPE: DNA
<213> ORGANISM: Artificial sequence
<220> FEATURE:
<223> OTHER INFORMATION: Sigma factor

<400> SEQUENCE: 19
atgggcagca gccatcatca tcatcatcac agcagcggcc tggaagttct gttccagggg       60
ccccatatga atgaaaccga tcctgatctg gaactgctga acgtattgg taataatgat       120 gcacaggccg ttaaagaaat ggttacccgt aaactgcctc gtctgctggc actggcaagt      180
cgcctgctgg gtgatgcaga tgaagcacgt gatattgcac aagaaagttt tctgcgcatt      240
tggaaacagg cagcaagctg gcgtagcgaa caggcacgtt ttgatacctg ctgcatcgt      300 gttgcactga atctgtgtta tgatcgtctg cgtcgtcgta aagaacatgt gccggttgat      360
agcgaacatg cctgtgaagc actggatacc cgtccggcac cggatgaaca gctggaagca      420
agcgcacaga gccgtcgtat ggcacaggca ctggatcagc tgccggatcg tcagcgtgaa      480
gcaattgttc tgcagtatta tcaagaactg agcaataccg aagcagcagc actgatgcaa      540
attagcgttg aagccctgga aagcctgctg agccgtgcac gtcgtaatct gcgtagccat      600
ctggccgaag caccgggtgc agatctgagc ggtcgtcgca aaccgtaa                   648
```